US006772084B2

(12) United States Patent
Bischoff et al.

(10) Patent No.: US 6,772,084 B2
(45) Date of Patent: Aug. 3, 2004

(54) OVERLAY MEASUREMENTS USING PERIODIC GRATINGS

(75) Inventors: Joerg Bischoff, Ilmenau (DE); Xinhui Niu, Los Altos, CA (US); Nickhil Jakatdar, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 171 days.

(21) Appl. No.: 10/066,555

(22) Filed: Jan. 31, 2002

(65) Prior Publication Data

US 2003/0212525 A1 Nov. 13, 2003

(51) Int. Cl.[7] .................................................. G03F 9/00
(52) U.S. Cl. ...................... 702/127; 382/144; 382/151; 356/400; 430/22
(58) Field of Search ................................ 356/400, 494, 356/499, 509; 430/22; 382/144, 151; 702/127; 250/548

(56) References Cited

U.S. PATENT DOCUMENTS

| | | | |
|---|---|---|---|
| 4,332,473 A | 6/1982 | Ono | |
| 4,631,416 A | * 12/1986 | Trutna, Jr. | ................... 250/548 |
| 4,929,083 A | 5/1990 | Brunner | |
| 5,347,356 A | 9/1994 | Ota et al. | |
| 5,452,090 A | 9/1995 | Progler et al. | |
| 5,468,580 A | 11/1995 | Tanaka | |
| 5,545,593 A | 8/1996 | Watkins et al. | |
| 5,559,598 A | * 9/1996 | Matsumoto | ................. 356/490 |
| 5,622,796 A | 4/1997 | Canestrari et al. | |
| 5,672,520 A | 9/1997 | Natsume | |
| 5,674,650 A | 10/1997 | Dirksen et al. | ................ 430/22 |
| 5,795,687 A | 8/1998 | Yasuda | ......................... 430/22 |
| 6,079,256 A | 6/2000 | Bareket | |
| 6,383,888 B1 | 5/2002 | Stirton | ......................... 430/22 |
| 6,457,169 B1 | 9/2002 | Ross | ............................. 716/4 |
| 6,489,068 B1 | 12/2002 | Kye | ............................ 382/144 |
| 2002/0158193 A1 | 10/2002 | Sezginer et al. | ............. 356/401 |
| 2003/0002043 A1 | 1/2003 | Abdulhalim et al. | ........ 356/400 |

FOREIGN PATENT DOCUMENTS

| | | |
|---|---|---|
| DE | 19925831 A1 | 12/2000 |
| EP | 0 272 853 A2 | 6/1988 |
| EP | 0 281 030 A2 | 9/1988 |
| EP | 0 422 395 A2 | 4/1991 |
| EP | 0 634 702 A1 | 1/1995 |
| WO | 97/45773 | 12/1997 |
| WO | 02/25723 A2 | 3/2002 |

OTHER PUBLICATIONS

Neal T. Sullivan, Semiconductor Pattern Overlay, 15 pages, Digital Equipment Corp., Advanced Semiconductor Development, Hudson, MA 01749–2895.

Lifeng, Li "Symmetries of Cross–Polarization Diffraction Coefficients of Gratings" *J. Opt. Soc. Am. A*/vol. 17, No. 5 (2000).

Bischoff, J. et al. "Light Diffraction Based Overlay Measurement" *Proc. SPIE* vol. 4344, pp. 222–233, *Metrology, Inspection, and Process Control for Microlithography XV*, (2001).

\* cited by examiner

*Primary Examiner*—Kamini Shah
(74) *Attorney, Agent, or Firm*—Morrison & Foerster LLP

(57) ABSTRACT

Overlay measurements for a semiconductor wafer are obtained by forming a periodic grating on the wafer having a first set of gratings and a second set of gratings. The first and second sets of gratings are formed on the wafer using a first mask and a second mask, respectively. The first and second sets of gratings are intended to be formed on the wafer with an intended asymmetrical alignment. A diffraction signal of the first and second sets of gratings is measured after the first and second sets of gratings are formed on the wafer. The misalignment between the first and second sets of gratings formed on the wafer is determined based on the measured diffraction signal.

91 Claims, 27 Drawing Sheets

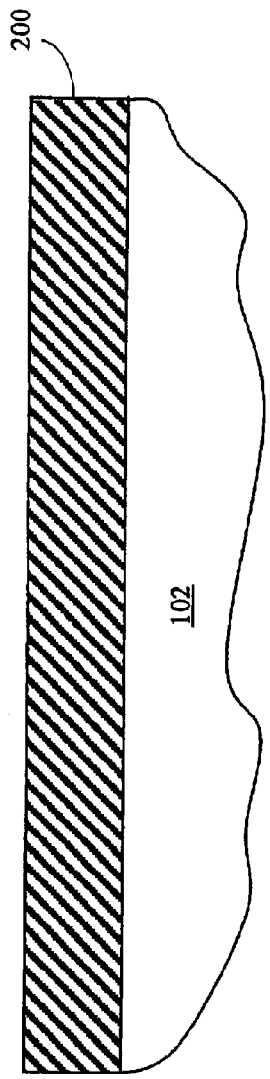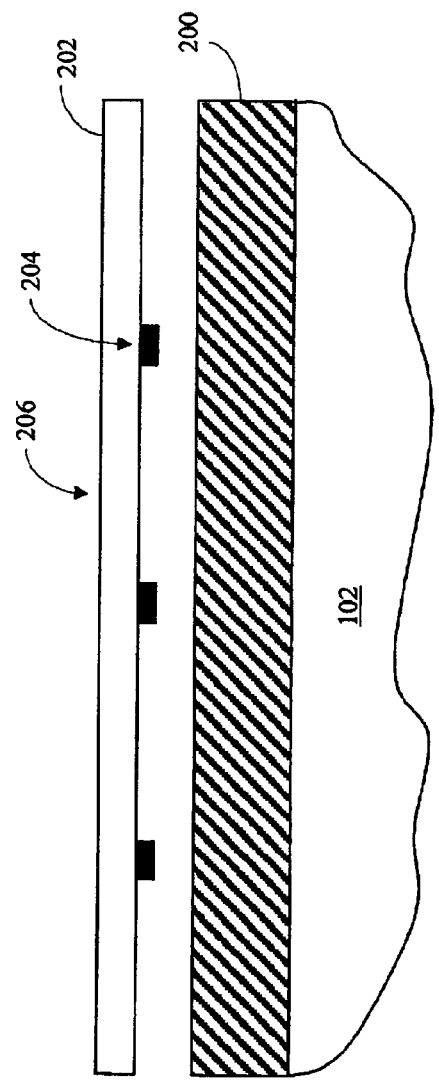

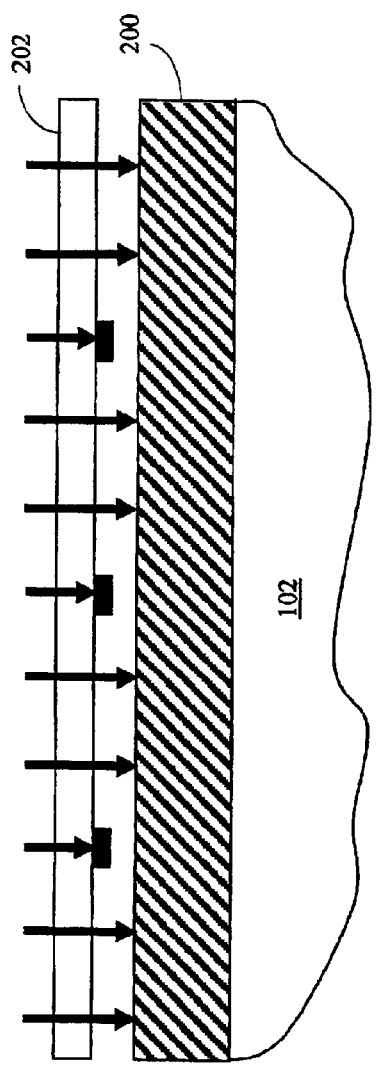
Fig. 2-C
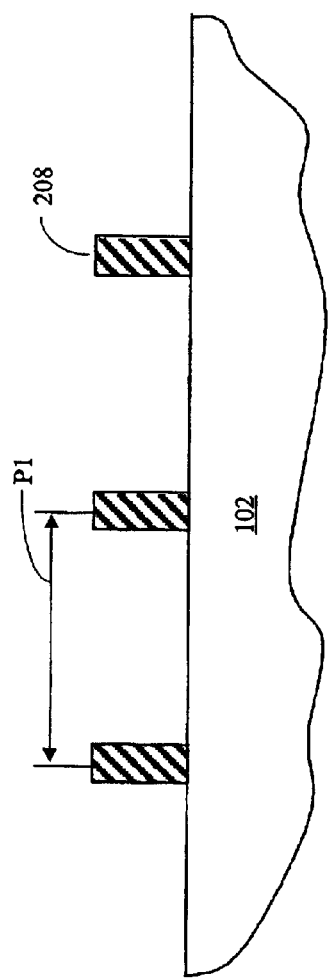
Fig. 2-D

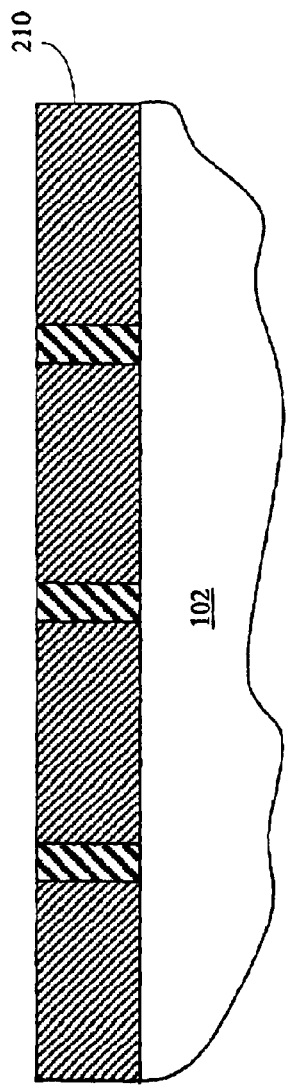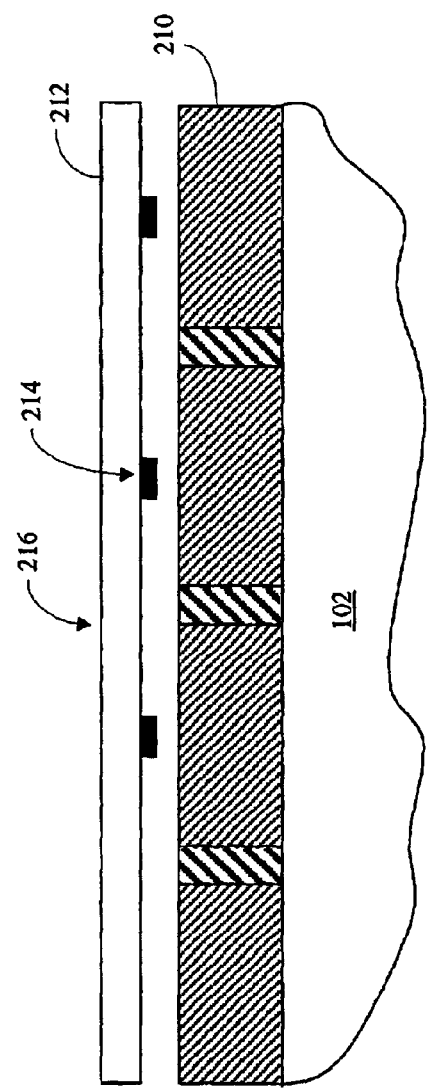

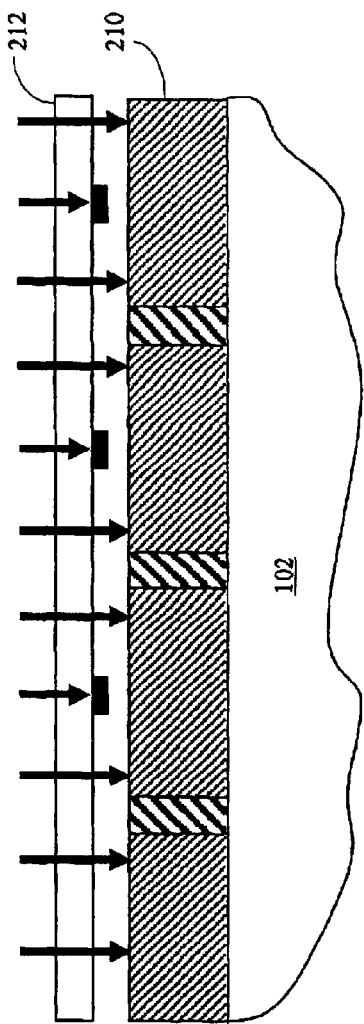
*Fig. 2-G*
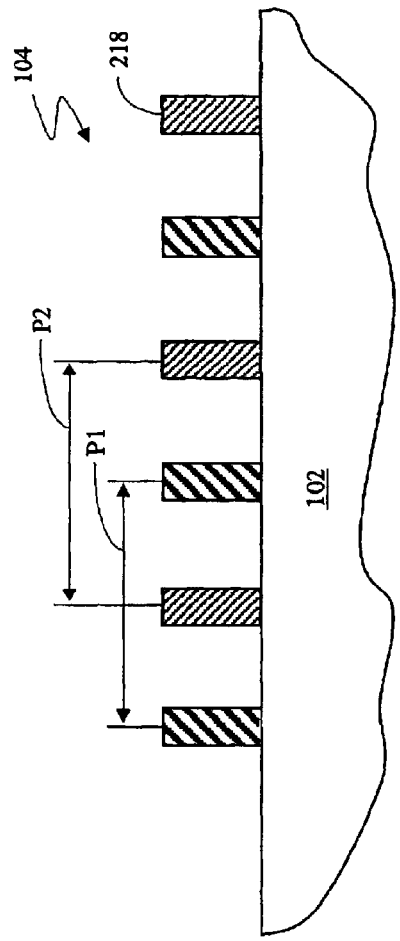
*Fig. 2-H*

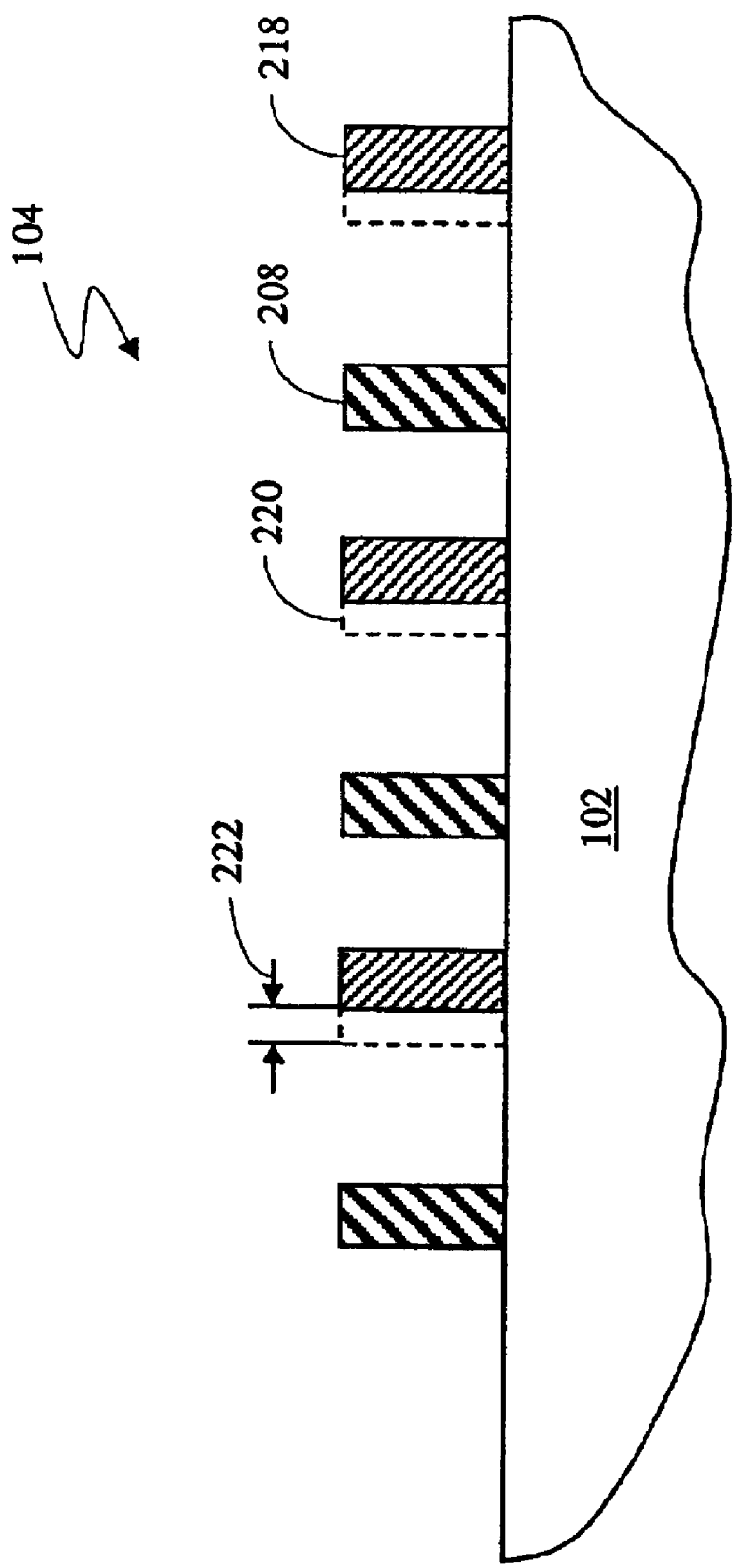
Fig. 2-I

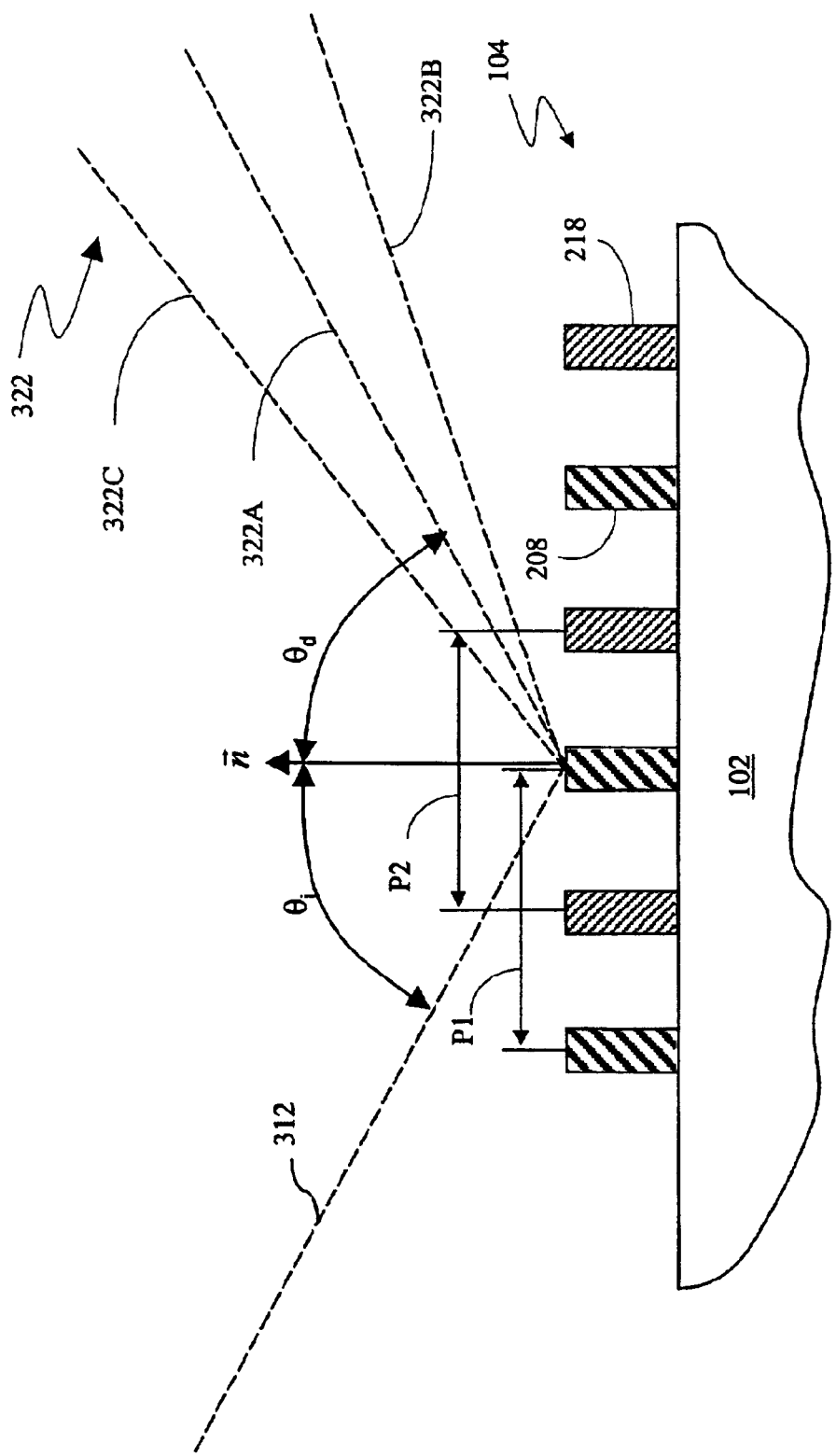
Fig. 4-A

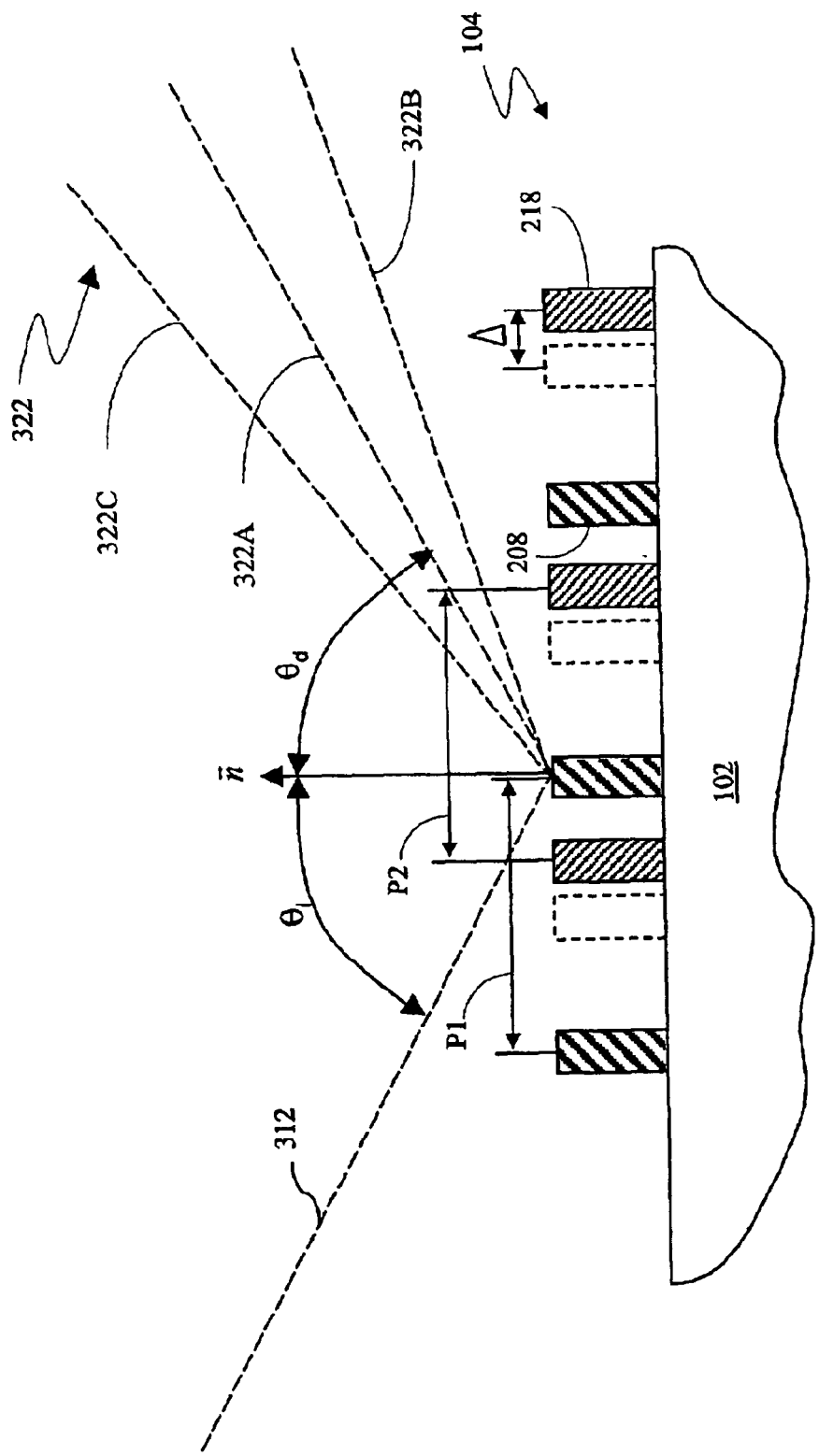
Fig. 4-B

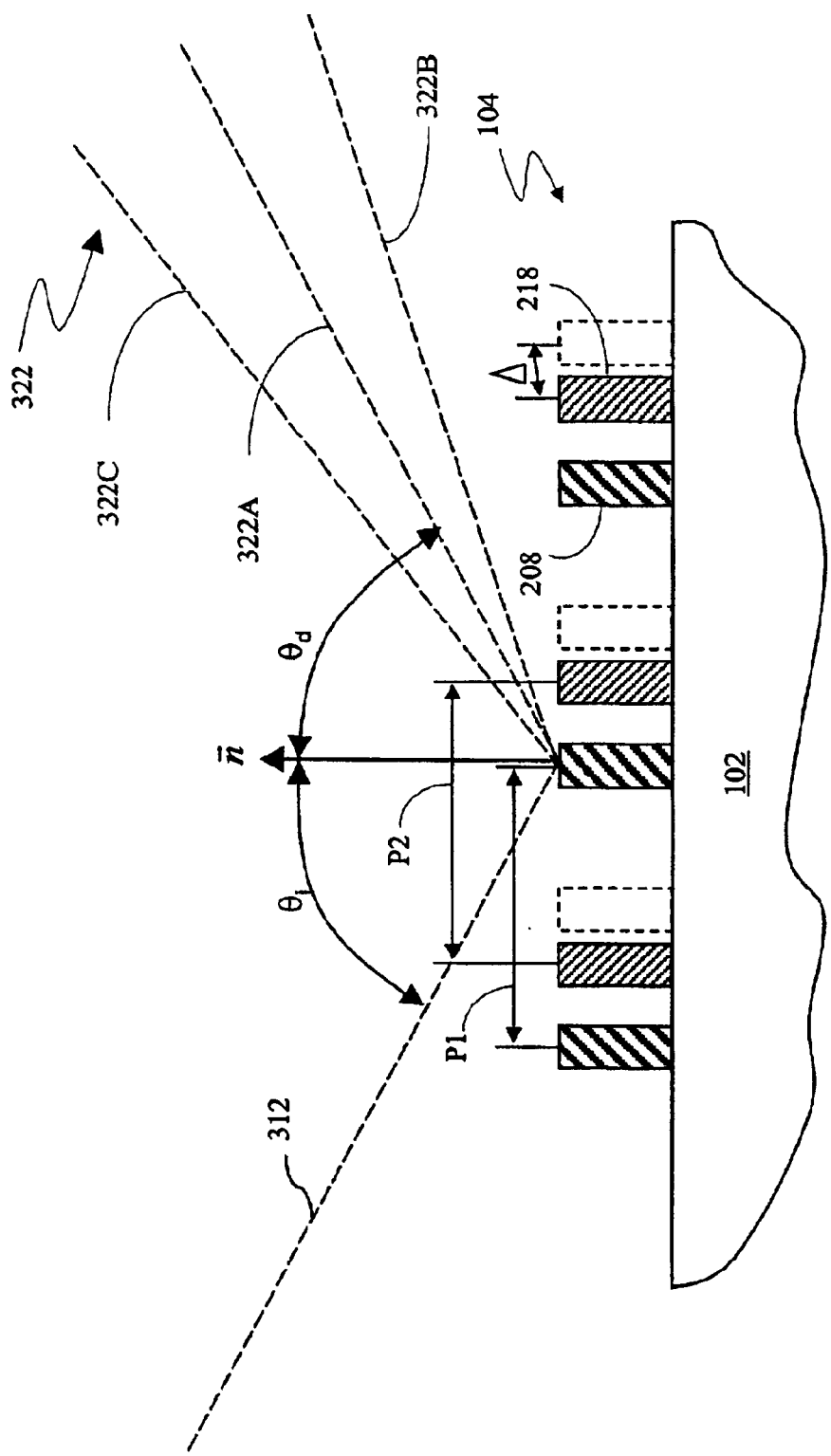
Fig. 4-C

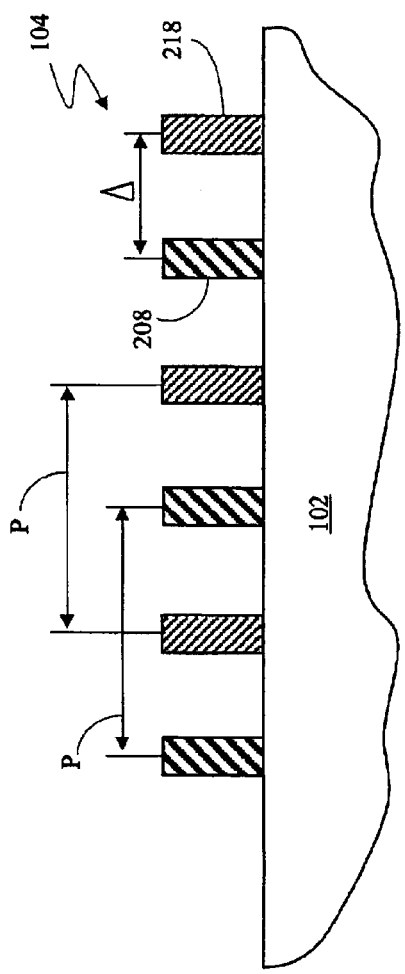
Fig. 6-A
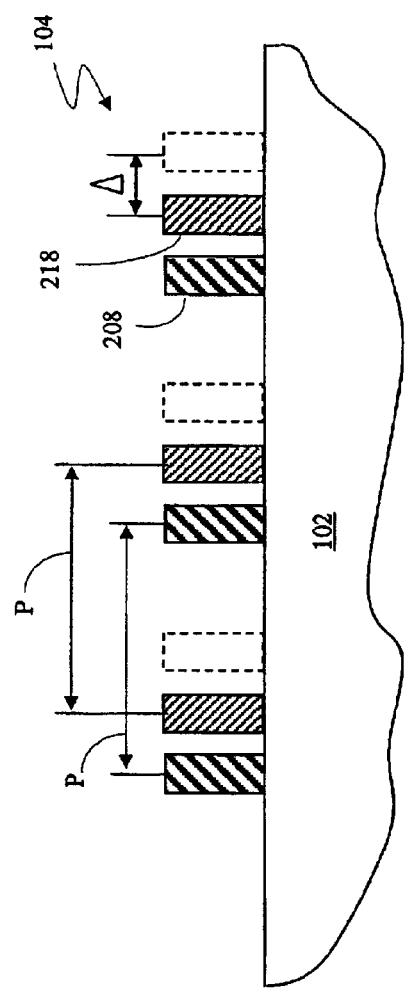
Fig. 6-B

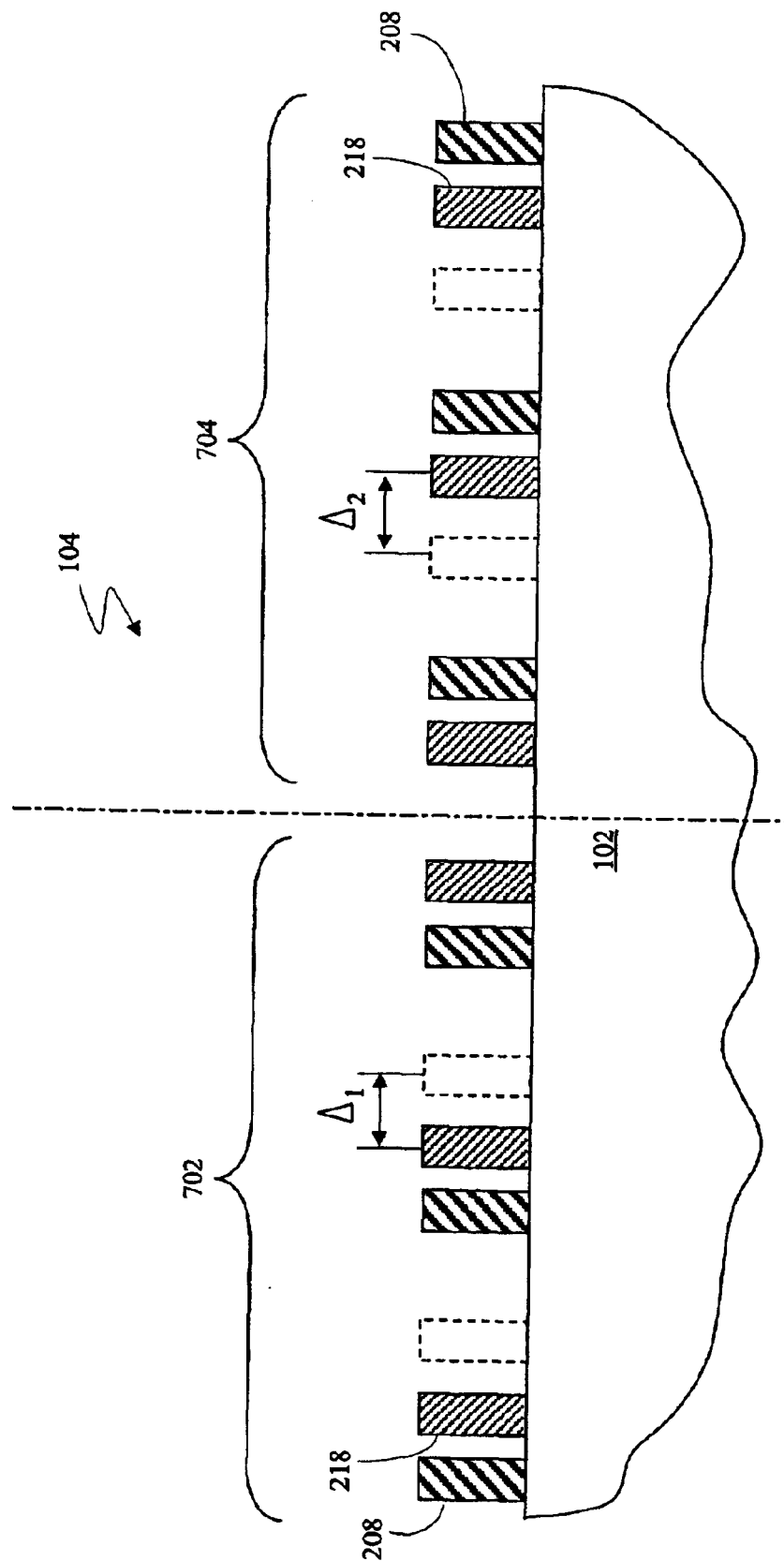

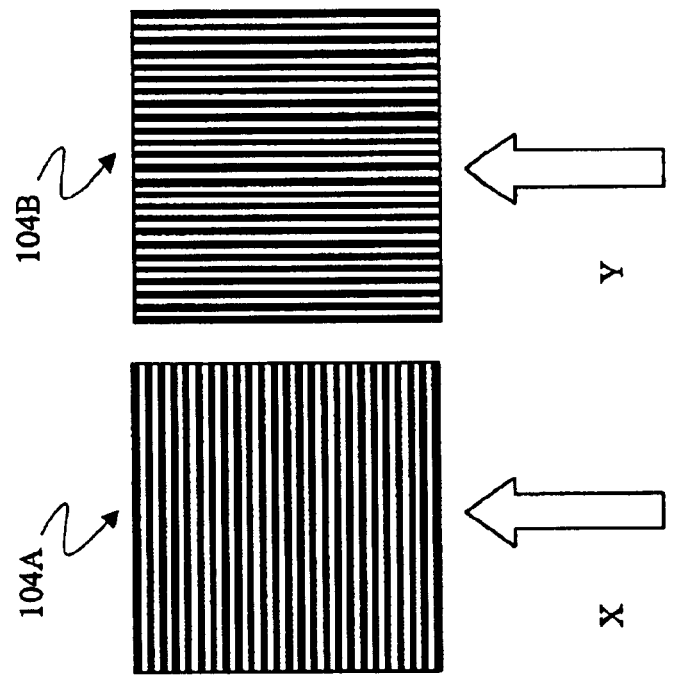
*Fig. 19-B*
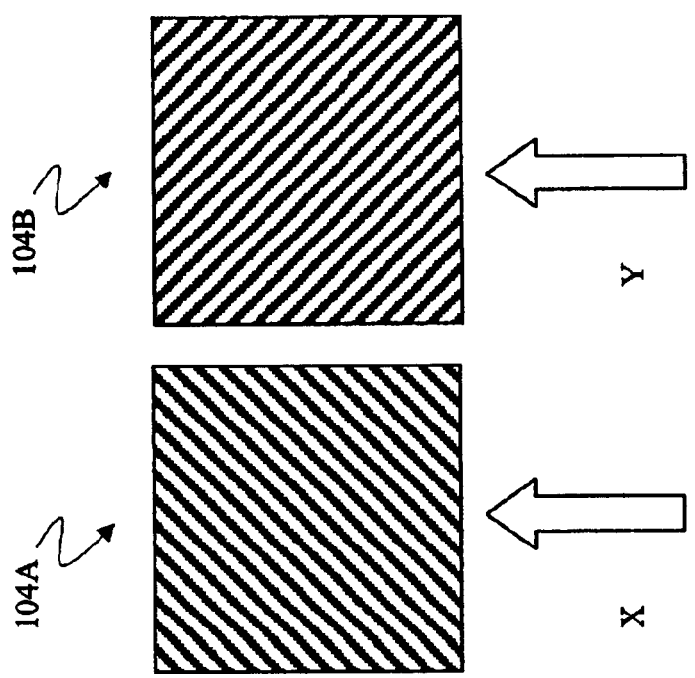
*Fig. 19-A*

OVERLAY MEASUREMENTS USING PERIODIC GRATINGS

BACKGROUND

1. Field of the Invention

The present invention relates to wafer metrology, and more particularly to obtaining overlay measurements for a semiconductor wafer using periodic gratings formed on the wafer.

2. Related Art

Semiconductor devices/circuits are formed on semiconductor wafers by depositing and patterning layers of materials. In general, the features of the devices/circuits are formed onto the layers of deposited materials using a patterning process.

In a typical patterning process, the features of the devices/circuits are laid out, one layer at a time, on a series of photomasks (masks). The layout of the features of the devices/circuits on the masks are transferred, one mask at a time, onto the deposited layers of materials. Misalignment of these masks, which is generally referred to as "overlay error", can adversely affect the performance of the devices/circuits.

To reduce overlay error, alignment marks, such as box-in-box or frame-in-frame overlay marks, are typically patterned onto the wafer and on layers deposited onto the wafer. At present, optical imaging systems are widely used to detect these alignment marks. However, a conventional optical imaging system typically has an accuracy of only about 5 to 10 nm. The continual shrinkage in the feature sizes of devices/circuits will likely require greater accuracy.

SUMMARY

In an exemplary embodiment, overlay measurements for a semiconductor wafer are obtained by forming a periodic grating on the wafer having a first set of gratings and a second set of gratings. The first and second sets of gratings are formed on the wafer using a first mask and a second mask, respectively. The first and second sets of gratings are intended to be formed on the wafer with an intended asymmetrical alignment. A diffraction signal of the first and second sets of gratings is measured after the first and second sets of gratings are formed on the wafer. The misalignment between the first and second sets of gratings formed on the wafer is determined based on the measured diffraction signal.

DESCRIPTION OF DRAWING FIGURES

The present invention can be best understood by reference to the following description taken in conjunction with the accompanying drawing figures, in which like parts may be referred to by like numerals:

FIG. 1 depicts an exemplary semiconductor wafer;

FIGS. 2-A to 2-I depict an exemplary process of forming a periodic grating;

FIG. 3 depicts an exemplary optical metrology system;

FIGS. 4-A to 4-C depict a portion of an exemplary periodic grating;

FIGS. 6A and 6B depict a portion of an exemplary periodic grating;

FIG. 7 depicts a portion of another exemplary periodic grating;

FIGS. 19-A and 19-B depict top views of exemplary periodic gratings; and

Figure 20:
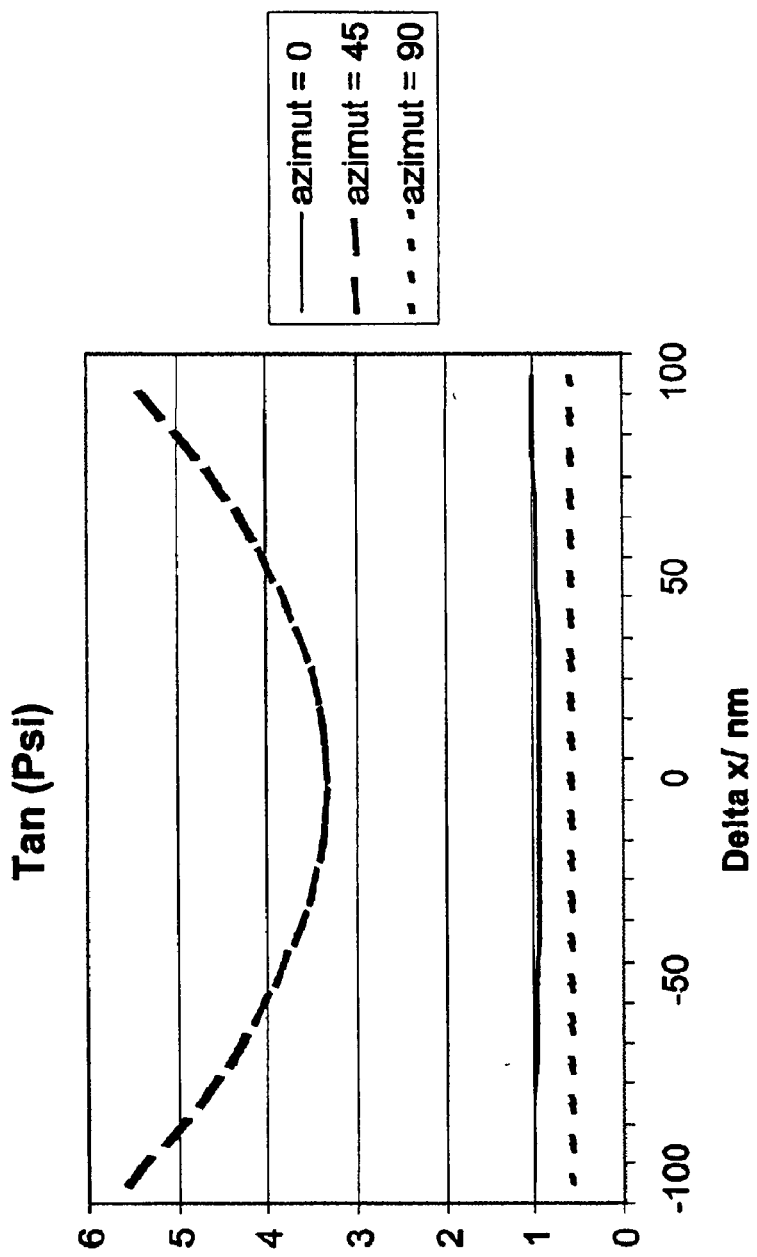
Figure 21:
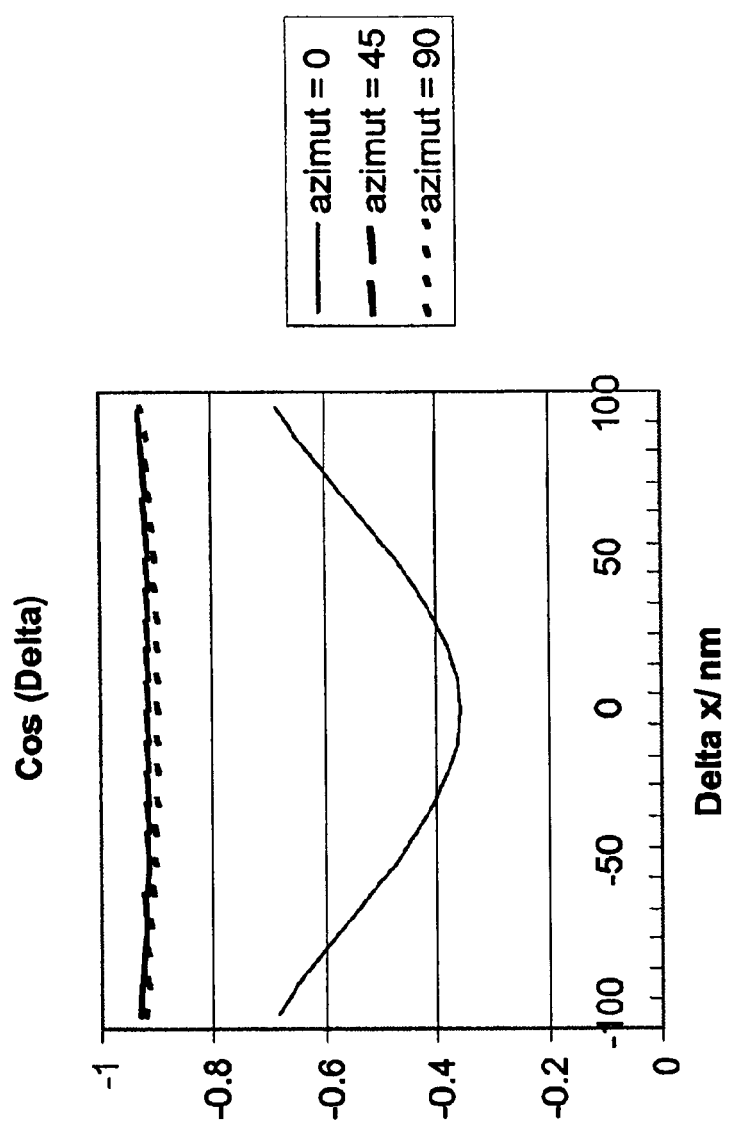

FIGS. 20 and 21 depict exemplary response curves.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
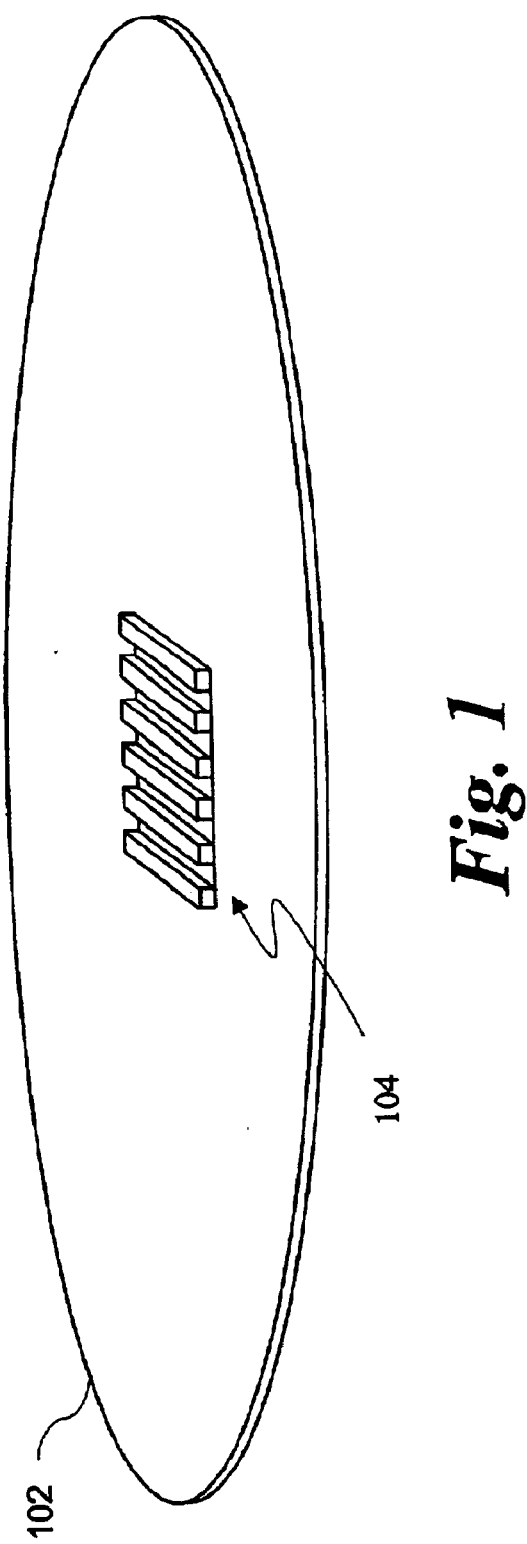

With reference to FIG. 1, as discussed earlier, the process of fabricating semiconductor devices/circuits on wafer 102 includes depositing and patterning layers of materials on wafer 102. More particularly, the features of the semiconductor devices/circuits are formed one layer at a time by depositing a layer of material, then removing portions of the deposited layer of material.

The process of depositing the layers of material is generally referred to as a deposition process. Exemplary deposition processes include chemical vapor deposition (CVD), oxidation, spin coating, sputtering, and the like. Exemplary materials that are deposited include oxides, metals, and the like.

The process of forming features on the deposited layers of materials is generally referred to as a patterning process, which typically includes a photolithography process and an etching process. More particularly, in a typical lithographic process, the features of the semiconductor device/circuit is laid out one layer at a time on a series of photomasks (masks). A single mask typically includes the layout for one layer of one or more chips throughout wafer 102.

As described above, multiple layers are typically deposited and patterned to form the features of semiconductor devices/circuits. As such, in forming these multiple layers, each mask, which corresponds to each layer, is aligned to properly form the features of the devices/circuits. Misalignment of the mask is typically referred to as an "overlay error." As noted earlier, overlay error can adversely affect the performance of the devices/circuits.

As will be described in greater detail below, an overlay measurement, which is a measure of overlay error, can be obtained using a periodic grating 104 formed on wafer 102. More particularly, as the features of the devices/circuits are formed on wafer 102 through the fabrication process described above, the features of periodic grating 104 are also formed on wafer 102. Thus, periodic grating 104 can be examined to obtain overlay measurements for wafer 102.

More particularly, one or more periodic gratings 104 can be formed in test areas on wafer 102 that are proximate to or within devices/circuits formed on wafer 102. For example, periodic grating 104 can be formed adjacent a device/circuit formed on wafer 102. Alternatively, periodic grating 104 can be formed in an area of the device/circuit that does not interfere with the operation of the device/circuit. Thus, the overlay measurements obtained for periodic grating 104 can be used to determine whether the devices/circuits adjacent periodic grating 104 have been fabricated according to specifications.

With reference now to FIGS. 2-A through 2-H, an exemplary fabrication process is depicted for forming periodic grating 104 (FIG. 1) on wafer 102. As noted above, the fabrication process that forms periodic grating 104 (FIG. 1) can also form devices/circuits of one or more chips throughout wafer 102. It should be noted that the following description is intended to be illustrative rather than comprehensive. As such, periodic grating 104 (FIG. 1) can be formed on wafer 102 with fewer or more process steps.

With reference to FIG. 2-A, a first layer 200 is deposited on wafer 102. For the purpose of this example, assume that first layer 200 is a photoresist layer. However, as noted earlier, first layer 200 can include various materials, such as oxides, metals, and the like.

With reference to FIG. 2-B, a first mask 202 is positioned above wafer 100 and first layer 200. First mask 202 includes portions 204 that block light and portions 206 that transmit light. Portions 204 of first mask 202 that block light can be patterned to have the same shape as the features that are to be formed on first layer 200. These types of masks are generally referred to as "light field" masks. Alternatively, portions 206 of first mask 202 that transmit light can be patterned to have the same shape as the features that are to be formed on first layer 200. These types of masks are generally referred to as "dark field" masks. For the sake of convenience and clarity, first mask 202 is depicted and described as being a "light field" mask.

With reference to FIG. 2-C, first mask 202 is aligned relative to wafer 102 such that the features that are to be formed on first layer 200 are positioned in the proper intended location. When first mask 202 is properly aligned, first mask 202 and portions of first layer 200 are exposed to light. As depicted in FIG. 2-C, only certain portions of first layer 200 are exposed to the light, i.e., the portions under portions 206 (FIG. 2-B) of first mask 202 that transmit light.

As described above, in this example, first layer 200 is a photoresist layer, which has the material characteristic that its solubility is responsive to exposure to light. More particularly, some photoresist change from a soluble to an insoluble condition when exposed to light. These types of photoresist are generally known as "negatively acting" resist. In contrast, some photoresist change from an insoluble to a soluble condition when exposed to light. These types of photoresist are generally known as "positively acting" resist. For the sake of convenience and clarity, assume that first layer 200 is a "positively acting" resist.

As such, with reference now to FIG. 2-D, when first layer 200 is exposed to an appropriate chemical solvent (i.e., a developer), the portions of first layer 200 that were exposed to the light are dissolved. Thus, in the present example, the remaining portions of first layer 200 form ridges 208 of periodic grating 104 (FIG. 1). As depicted in FIG. 2-D, ridges 208 are spaced regularly with a period of P1.

It should be noted that first mask 202 (FIG. 2-B) can be patterned to include the shapes of the features of one layer of the devices/circuits that are to be formed on wafer 102 (FIG. 1), and more particularly on first layer 200. As such, during the process of forming ridges 208 of periodic grating 104 (FIG. 1), the features of one layer of devices/circuits are also being formed on first layer 200 of one or more chips throughout wafer 102.

With reference now to FIG. 2-E, assume now that a second layer 210 is deposited. For the purpose of this example, assume that second layer 210 is also a photoresist layer. However, as noted earlier, second layer 210 can include various materials, such as oxides, metals, and the like. Additionally, it should be noted that FIG. 2-E, similar to all the figures, is intended to be illustrative rather than realistic. For example, although in FIG. 2-E the topology of second layer 210 is depicted as being flat, it is typically uneven.

With reference now to FIG. 2-F, a second mask 212 is positioned above wafer 102 and second layer 212. Similar to first mask 202 (FIG. 2-A), assume for the sake of this example that second mask 212 is also a "light field" mask. As such, portions 214 of second mask 212 that block light are patterned to have the same shape as the features that are to be formed on second layer 210. However, similar to first mask 202 (FIG. 2-A), portions 216 of second mask 212 that transmit light can be patterned to have the same shape as the features that are to be formed on second layer 210.

With reference to FIG. 2-G, second mask 212 is aligned relative to wafer 102 such that the features that are to be formed on layer 210 are positioned in the proper location. When second mask 212 is properly aligned, second mask 212 and portions of layer 210 are exposed to light. As depicted in FIG. 2-G, only certain portions of layer 210 are exposed to the light, i.e., the portions under portions 216 (FIG. 2-F) of second mask 212 that transmit light.

Similar to first layer 200 (FIG. 2-A), assume for the sake of this example that second layer 210 is formed from a "positively acting" resist. As such, with reference now to FIG. 2-G, when second layer 210 is exposed to an appropriate chemical solvent (i.e., a developer), the portions of second layer 210 that were exposed to the light are dissolved. Thus, in the present example, the remaining portions of second layer 210 form ridges 218 of periodic grating 104 (FIG. 1). As depicted in FIG. 2-F, ridges 218 are spaced regularly with a period of P2.

It should be noted that second mask 212 (FIG. 2-B) can be patterned to include the shapes of the features of another layer of the devices/circuits that are to be formed on wafer 102 (FIG. 1), and more particularly on second layer 210. As such, during the process of forming ridges 218 of periodic grating 104 (FIG. 1), the features of another layer of devices/circuits are also being formed on second layer 210 of one or more chips throughout wafer 102.

As noted earlier, misalignment of first mask 202 (FIG. 2-B) and/or second mask 212 (FIG. 2-F) can produce "overlay error." For example, with reference now to FIG. 2-I, assume that due to a misalignment of second mask 212 (FIG. 2-F) with respect to first mask 202 (FIG. 2-B), the location of ridges 218 is shifted from its proper intended location. In FIG. 2-I, assume that dotted outlines 220 depict the proper intended location of ridges 218. As such, offset 222 indicates the amount by which ridges 218 have been shifted from their intended position. Thus, offset 222 represents the "overlay error" that has occurred.

As noted above, as ridges 208 and 218 of periodic grating 104 (FIG. 1) are formed using first mask 202 (FIG. 2-B) and second mask 212 (FIG. 2-F), the features of two layers of devices/circuits are also being formed on one or more chips throughout wafer 102 (FIG. 1). As such, a misalignment of second mask 212 (FIG. 2-F) produces a shift in the location of the features of the second layer of the devices/circuits formed on second layer 210 (FIG. 2-E) relative to the features of the first layer of the devices/circuits formed on first layer 200 (FIG. 2-A).

Although ridges 208 and 218 have been depicted and described as being formed directly on wafer 102, it should be noted that ridges 208 and 218 can be formed on an intermediate layer formed on wafer 102.

As also noted above, periodic grating 104 (FIG. 1) is formed adjacent devices/circuits formed on wafer 102 (FIG. 1). As such, overlay measurements (i.e., the measurement of the overlay error) of periodic grating 104 (FIG. 1) can be used to determine whether an overlay error exists in the devices/circuits adjacent periodic grating 104 (FIG. 1).

Furthermore, as noted above, a single mask typically includes the layout of one layer of one more chips on wafer 102 (FIG. 1). For example, first mask 202 (FIG. 2-B) includes the layout for first layer 200 (FIG. 2-B) of one or more chips on wafer 102 (FIG. 1). Second mask 212 (FIG. 2-F) includes the layout for second layer 210 (FIG. 2-F) of one or more chips on wafer 102 (FIG. 1). As such, overlay measurements of periodic grating 104 (FIG. 1) can be used to determine whether an overly error exists in the devices/circuits of one or more chips throughout wafer 102 (FIG. 1).

Figure 3:
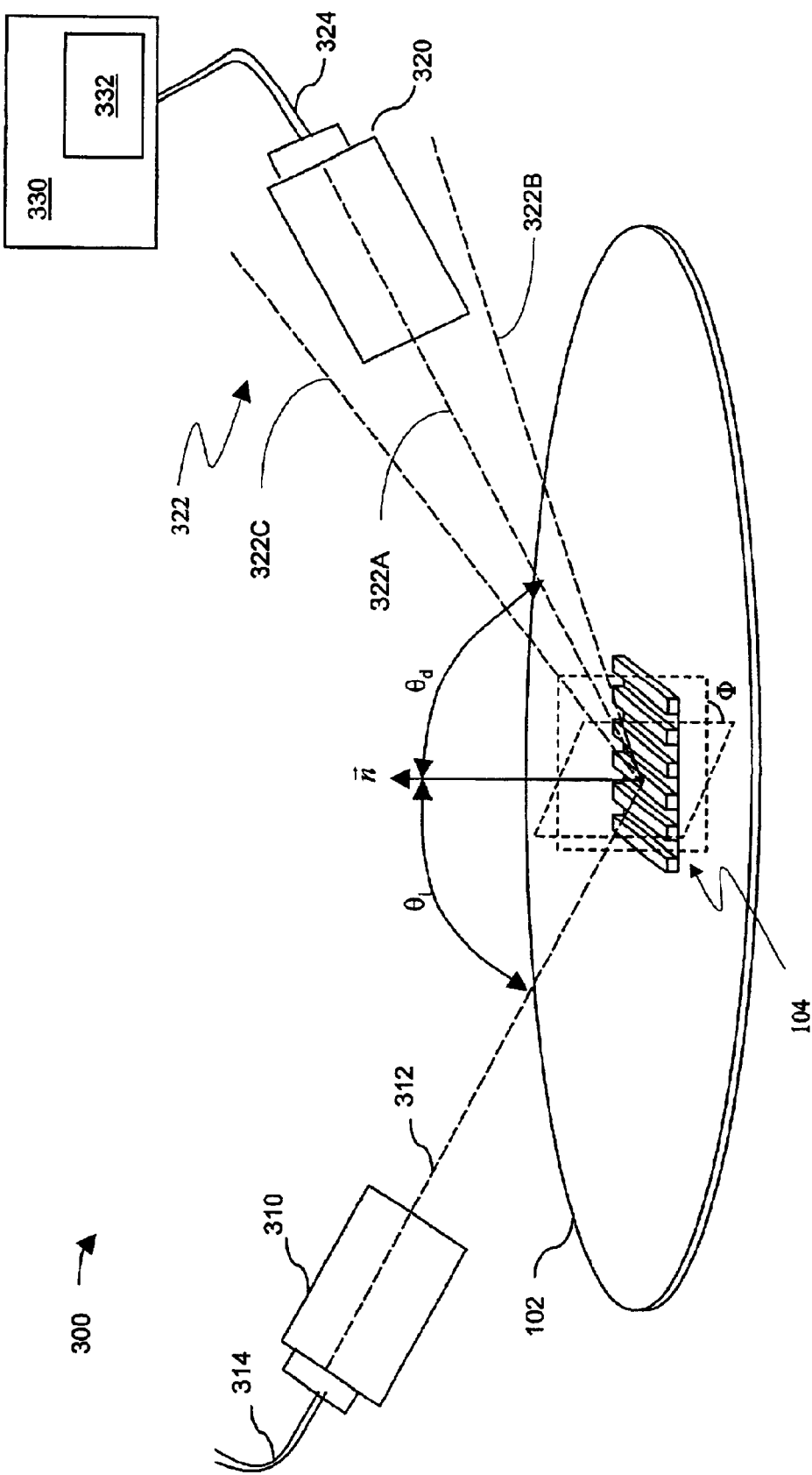

With reference now to FIG. 3, an optical metrology system 300 can be configured to examine periodic grating 104 to obtain overlay measurements. More particularly, as depicted in FIG. 3, optical metrology system 300 includes an electromagnetic source 310. Periodic grating 104 is illuminated by an incident signal 312 from electromagnetic source 310. Electromagnetic source 310 can include focusing optics to control the spot size of incident signal 312. In one embodiment, spot size of incident signal 312 can be reduced to less than the size of the test area on wafer 102 that contains periodic grating 104. For example, a spot size of about 50 μm by 50 μm, or smaller, can be used. Additionally, electromagnetic source 310 can include a pattern recognition module to center the spot in the test area on wafer 102. Furthermore, electromagnetic source 310 can include a polarizing element such as a polarizer.

As depicted in FIG. 3, incident signal 312 is directed onto periodic grating 104 at an angle of incidence $\theta_i$ with respect to normal $\vec{n}$ of periodic grating 304. The angle of incidence $\theta_i$ can vary depending on the application. For example, in one exemplary embodiment, the angle of incidence $\theta_i$ is between about 0 and about 90 degrees. In another embodiment, the angle of incidence $\theta_i$ is between about 30 and about 90 degrees. In still another embodiment, the angle of incidence $\theta_i$ is between about 40 and about 75 degrees. In yet another embodiment, the angle of incidence $\theta_i$ is between about 50 and about 70 degrees.

As depicted in FIG. 3, diffraction signal 322 leaves at an angle of $\theta_d$ with respect to normal $\vec{n}$. More particularly, diffraction signal 322 includes a plurality of diffraction orders. For the sake of illustration and clarity, FIG. 3 depicts diffraction signal 322 having a zero-order diffraction (diffraction signal 322A), a positive first-order diffraction (diffraction signal 322B), and a negative first-order diffraction (diffraction signal 322C). It should be recognized, however, that diffraction signal 322 can include any number of diffraction orders.

Diffraction signal 322 is received by detector 320 and analyzed by signal-processing system 330. When optical metrology system 300 includes an ellipsometer, the magnitude ratio $\Psi$ and the phase $\Delta$ of diffraction signal 322 is received and detected. When optical metrology system 300 includes a reflectometer, the relative intensity of diffraction signal 322 is received and detected. Additionally, detector 320 can include a polarizing element such as an analyzer.

With reference now to FIG. 4-A, as noted earlier, ridges 208 and 218 of periodic grating 104 have periods of P1 and P2, respectively. Assume now that periods P1 and P2 are the same. Additionally, as depicted in FIG. 4-A, when ridges 208 and 218 are formed adjacent to each other, they can be symmetrically aligned such that the spacing between a ridge 218 and a ridge 208 on either side is equal. More particularly, ridges 208 and 218 are symmetrically aligned when the spacing between their centerlines is uniform, and asymmetrically aligned when the spacing between their centerlines is non-uniform or uneven.

When ridges 208 and 218 (FIG. 4-A) are symmetrically aligned, the positive and negative first-order diffractions (i.e., diffracted signals 322B and 322C) are equal. As such, misalignment of ridges 208 and 218 can be detected by measuring the difference between the positive and negative first-order diffractions and determining whether the difference is zero or non-zero.

For example, with reference to FIG. 4-B, assume that an overlay error exists and that ridges 218 are shifted to the right of their symmetric position. When diffracted signals 322B and 322C are detected and measured, the difference between the two signals is positive. In contrast, with reference to FIG. 4-C, if ridges 218 are shifted to the left of their symmetric position, the difference between the diffracted signals 322B and 322C is negative. As such, the direction of misalignment of ridges 208 and 218 can be detected by measuring the difference between the positive and negative first-order diffractions and determining whether the difference is positive or negative. However, the correlation between the direction of misalignment and the sign of the difference can depend on the materials. For example, the direction of misalignment can generally be determined using normal incidence based on the difference between the positive and negative first-order diffractions if ridges 208 and 218 are formed from the same material.

With reference again to FIG. 3, the positive and negative first-order diffractions (i.e., diffracted signals 322B and 322C) can be detected using additional detectors 320. Alternatively, diffracted signals 322B and 322C can be detected using a single detector 320 by moving detector 320.

In one exemplary embodiment, rather than using the positive and negative first-order diffractions, the zero-order diffraction (i.e., reflection) is used to obtain overlay measurements. More particularly, in the present embodiment, only the zero-order diffraction (i.e., diffraction signal 322A) is used to determine the amount and direction of overlay errors.

Figure 5:
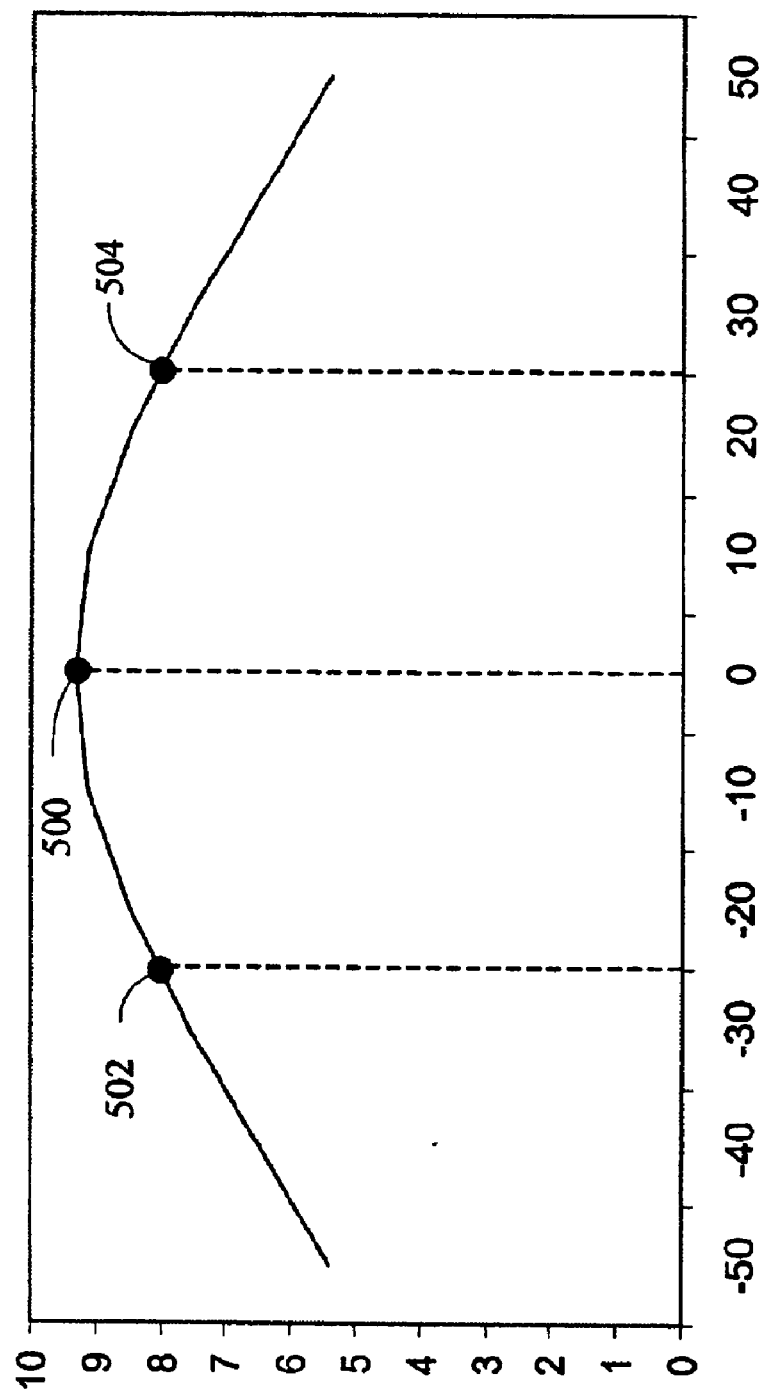
FIG. 5 is an exemplary curve of misalignment of gratings and diffractions.

With reference to FIG. 5, an exemplary response curve of the efficiency of the zero-order diffraction signal (diffraction) versus various misalignments of ridges 208 and 218 (FIG. 6-A) is depicted. In FIG. 5, a misalignment of zero (i.e., point 0 on the horizontal axis) corresponds to symmetric alignment between ridges 208 and 218 (i.e., when the spacing between a ridge 218 and a ridge 208 on either side is equal, as depicted in FIG. 4-A). Positive misalignment (i.e., a point to the right of 0 on the horizontal axis) corresponds to ridge 218 shifted to the right of its symmetric alignment position (FIG. 4-B). Negative misalignment (i.e., a point to the left of 0 on the horizontal axis) corresponds to ridge 218 shifted to the left of its symmetric alignment position (FIG. 4-C).

Thus, in FIG. 5, point 500 corresponds to symmetric alignment of ridges 208 and 218 (FIG. 6-A). As depicted in FIG. 5, point 500 corresponds to a unique combination of diffraction (i.e., a point on the vertical axis) and misalignment (i.e., a point on the horizontal axis). As such, point 500 can be used to detect the existence of an overlay error. However, as also depicted in FIG. 5, for all points other than point 500, there are two possible misalignments for each diffraction. As such, if point 500, which corresponds to a symmetric alignment of ridges 208 and 218 (FIG. 6-A), is used to determine when there is zero overlay error, and if an overlay error results, the direction of misalignment cannot be determined solely based on zero-order diffraction. Additionally, as depicted in FIG. 5, the curve is relatively insensitive (i.e., relatively flat) near point 500. Thus, small changes in misalignment from point 500 produce a relatively small change in diffraction, which can increase the difficulty of detecting the existence of an overlay error.

Therefore, in the present exemplary embodiment, with reference to FIG. 6-B, ridges 208 and 218 are intended to be formed asymmetrically aligned with respect to each other. More particularly, as depicted in FIG. 6-B, when ridges 208 and 218 are formed adjacent to each other, ridges 218 are formed with an intended asymmetric alignment (i.e., intentionally shifted from their symmetric alignment position). More particularly, in the present embodiment, ridges 218 are shifted by an intended asymmetric alignment (i.e., an offset) of about a quarter of period P (i.e., the period of ridges 208 and 218). It should be recognized, however, that various offsets can be utilized. Additionally, it should be noted that ridges 218 can be shifted to the right of their symmetric alignment position. Furthermore, rather than shifting only ridges 218, ridges 208 can be shifted instead, or both ridges 218 and 208 can be shifted.

With reference to FIG. 5, point 502 corresponds to shifting ridges 218 (FIG. 6-B) an offset of about a quarter period to the left of their symmetric alignment position. As depicted in FIG. 5, a unique combination of diffraction (i.e., points on the vertical axis) and misalignment (i.e., points on the horizontal axis) exist for a range of a quarter period to the left and to the right of point 502 (i.e., between −50 and 0 along the horizontal axis). As such, point 502, which corresponds to an asymmetrical alignment of ridges 208 and 218 (FIG. 6-B), can be used to detect the existence and amount of an overlay error and the direction of misalignment between zero period and half period.

As noted earlier, although an offset of about a quarter of a period to the left was depicted and described above, various offsets can be selected. For example, with reference again to FIG. 5, point 504, which corresponds to an offset of about a quarter of a period to the right, can be selected. As such, if it is known or suspected that the overlay error tends to occur more in one direction than another, then an appropriate offset can be selected to compensate for the tendency. For example, with reference to FIG. 6-B, assume that it is known that ridges 218 tend to be misaligned more to the right of their intended positions. In this case, it may be desirable to select an offset that is more than about a quarter of a period to the left, which corresponds to points to the left of point 502 in FIG. 5.

As described above, by asymmetrically aligning ridges 208 and 218 (FIG. 6-B), overlay measurements can be obtained based solely on measured zero-order diffractions. More particularly, ridges 208 and 218 are intended to be formed asymmetrically aligned with an offset. After ridges 208 and 218 are formed, optical metrology system 300 (FIG. 3) can be used to obtain diffraction measurements of ridges 208 and 218. The diffraction measurements can then be utilized to determine if ridges 208 and 218 were formed with the intended asymmetric alignment. Because ridges 208 and 218 are intended to be asymmetrically aligned, the diffraction measurements can be utilized to determine both the amount and direction of misalignment.

It should be recognized that the response curve depicted in FIG. 5 can be generated empirically or computed through modeling. Additionally, the relationship between misalignment and efficiency of the diffraction signal, as depicted in FIG. 5, can be stored as a function or as a table of data. Furthermore, this information can be accessed by optical metrology system 300 (FIG. 3) to obtain overlay measurements.

For example, with reference to FIG. 3, assume that one or more response curves similar to that depicted in FIG. 5 are generated and provided to metrology system 300. The response curves can be stored on a storage media, such as a hard drive, CD, and the like, or remotely accessed by optical metrology system 300. Additionally, as noted above, the response curves can be provided in various formats, such as a function, table of data, and the like.

Now assume that wafer 102 has been fabricated and that periodic grating 104 is to be examined to obtain overlay measurements. As described above, source 310 directs an incident signal at periodic grating 104. Detector 320 receives the first-order diffraction signal 322A. Signal-processing system 320 can then use the measured diffraction signal (i.e., the measured diffraction) and the response curve to obtain overlay measurements for periodic grating 104. For example, the measured diffraction can be compared with those on the response curve, and then the amount and direction of misalignment can be determined from the response curve. It should be noted, however, that various tools and techniques can be used to obtain overlay measurements from the measured diffraction and the response curve.

However, changes in the linewidth, height, or profile of ridges 208 and/or 218 (FIG. 6) can alter the response curve depicted in FIG. 5. As such, with reference to FIG. 7, in another exemplary embodiment, periodic grating 104 is configured to reduce the sensitivity to process and profile changes in obtaining overlay measurements. In the present embodiment, periodic grating 104 includes a subfield 702 and a subfield 704 that are mirror images of one another. More particularly, as depicted in FIG. 7, in subfield 702, ridges 218 are shifted to the left of their symmetric alignment position by an offset of $\Delta_1$. In subfield 704, ridges 218 are shifted to the right of their symmetric alignment position by an offset of $\Delta_2$, where $\Delta_1$ and $\Delta_2$ are equal in magnitude but opposite in sign. As before, ridges 208 have the same period as ridges 218.

In the present embodiment, ridges 218 are formed with an intentional asymmetric alignment (i.e., an offset) of about a quarter of the period of ridges 208 and 218. As before, it should be recognized, however, that various offsets can be utilized.

Additionally, in the present embodiment, ridges 208 are patterned with a uniform period throughout subfield 702 and subfield 704. In contrast, a set of ridges 218 having the same period as ridges 208 and with an offset of $\Delta_1$ are patterned in subfield 702, and a set of ridges 218 having the same period as ridges 208 and with an offset of $\Delta_2$ are patterned in subfield 704.

As before, ridges 208 and 218 can be patterned using separate masks. More particularly, ridges 208 can be patterned using one mask, and ridges 218 can be patterned using another mask. It should be noted, however, that ridges 208 and 218 can be formed in a variety of manners.

To obtain overlay measurements, zero-order diffraction signals ($S_1$ and $S_2$) are measured from subfield 702 and subfield 704. A difference signal is then computed that corresponds to the difference between these two signals (i.e., $S_{Diff}=S_1-S_2$). When the overlay error is zero, the difference signal is zero. With regard to subfield 702, when the overlay error is positive, which in the context of this example corresponds to ridges 208 being patterned left of their intended positions with respect to ridges 218 or ridges 218 being patterned right of their intended positions with respect to ridges 208, the difference signal is positive. With regard to subfield 702, when the overlay error is negative, which in the context of this example corresponds to ridges 208 being patterned right of their intended positions with respect to ridges 218 or ridges 218 being patterned left of their intended positions with respect to ridges 208, the difference signal is negative. Thus, the difference signal indicates the existence of an overlay error and the direction of misalignment. Moreover, as the difference signal is a difference between two signals and not an absolute value, it is less sensitive to process and profile changes in forming ridges 208 and 218.

Thus far, ridges 208 and 218 have been depicted as being pattered adjacent to each other. The proximity of ridges 208 to 218, however, can result in additional error in patterning ridges 218. This is generally known as "proximity error", and can reduce the accuracy of the overlay measurement.

Figure 8:
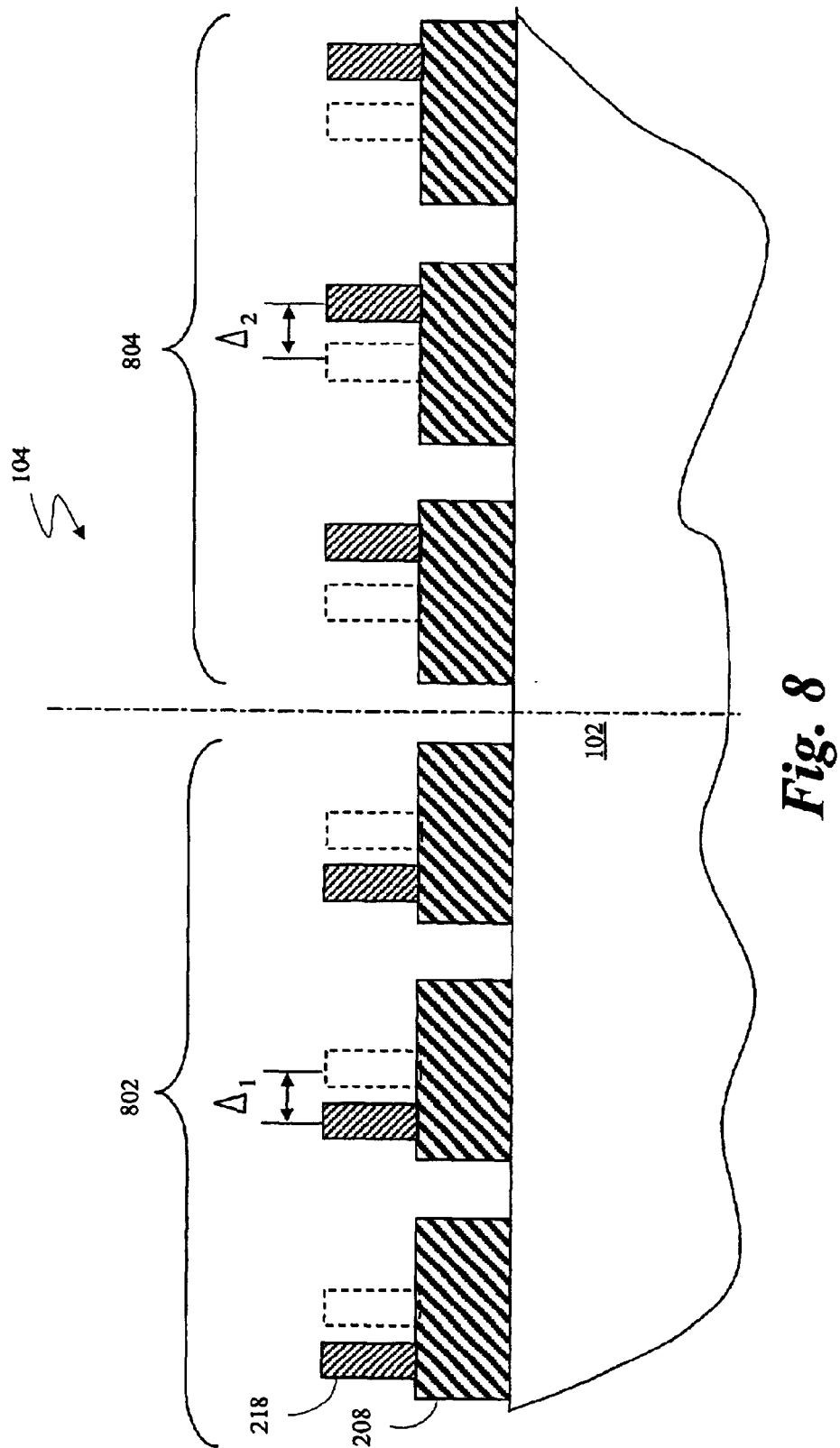
FIG. 8 depicts a portion of still another exemplary periodic grating.

Therefore, with reference to FIG. 8, in another exemplary embodiment, ridges 218 are patterned on ridges 208. In the present embodiment, ridges 218 and 208 are symmetrically aligned when the centerlines of ridges 218 and 208 are aligned. Thus, ridges 218 and 208 are asymmetrically aligned when the centerlines of ridges 218 and 208 are not aligned. As depicted in FIG. 8, in the present embodiment, the offset ($\Delta_1$ and $\Delta_2$) between ridges 218 and their symmetric alignment position also corresponds to the amount of misalignment between the centerlines of ridges 218 and 208.

As depicted in FIG. 8, in the present embodiment, the linewidth of ridges 208 is greater than the linewidth of ridges 218. Additionally, in the present embodiment, ridges 218 are formed with an intended asymmetric alignment (i.e., an intended offset) of about a quarter of the linewidth of ridges 208. As before, it should be recognized, however, that various offsets can be utilized. Additionally, the difference in the linewidth of ridges 208 and 218 determines the maximum range over which the offset ($\Delta_1$ and $\Delta_2$) between ridges 208 and 218 can be varied. Note that in addition to reducing proximity effect, this maximum range can be greater when ridges 218 are patterned on ridges 208 rather than adjacent ridges 208.

As described above, optical metrology system 300 (FIG. 3) can be used to obtain diffraction measurements of ridges 208 and 218. The diffraction measurements can then be utilized to determine if ridges 208 and 218 were formed with the intended offset. Because ridges 208 and 218 are intended to be asymmetrically aligned, the diffraction measurements can be utilized to determine both the amount and direction of misalignment.

Additionally, with reference again to FIG. 8, periodic grating 104 includes subfields 802 and 804 that are mirror images of one another. In subfield 802, ridges 218 are shifted to the left of their symmetric alignment position by an offset of $\Delta_1$. In subfield 804, ridges 218 are shifted to the right of their symmetric alignment position by an offset of $\Delta_2$, where $\Delta_1$ and $\Delta_2$ are equal in magnitude but opposite in sign.

To obtain overlay measurements, a zero-order diffraction signal is measurement from subfield 802 and subfield 804. A difference signal is then computed that corresponds to the difference between these two signals (i.e., $S_{Diff}=S_1-S_2$). When the overlay error is zero, the difference signal is zero. With regard to subfield 802, when the overlay error is positive, which in the context of this example corresponds to ridges 208 being patterned left of their intended positions with respect to ridges 218 or ridges 218 being patterned right of their intended positions with respect to ridges 208, the difference signal is positive. With regard to subfield 802, when the overlay error is negative, which in the context of this example corresponds to ridges 208 being patterned right of their intended positions with respect to ridges 218 or ridges 218 being patterned left of their intended positions with respect to ridges 208, the difference signal is negative. Thus, the difference signal indicates the existence of an overlay error and the direction of misalignment. Moreover, as the difference signal is a difference between two signals and not an absolute value, it is less sensitive to process and profile changes in forming ridges 208 and 218.

Figure 9:
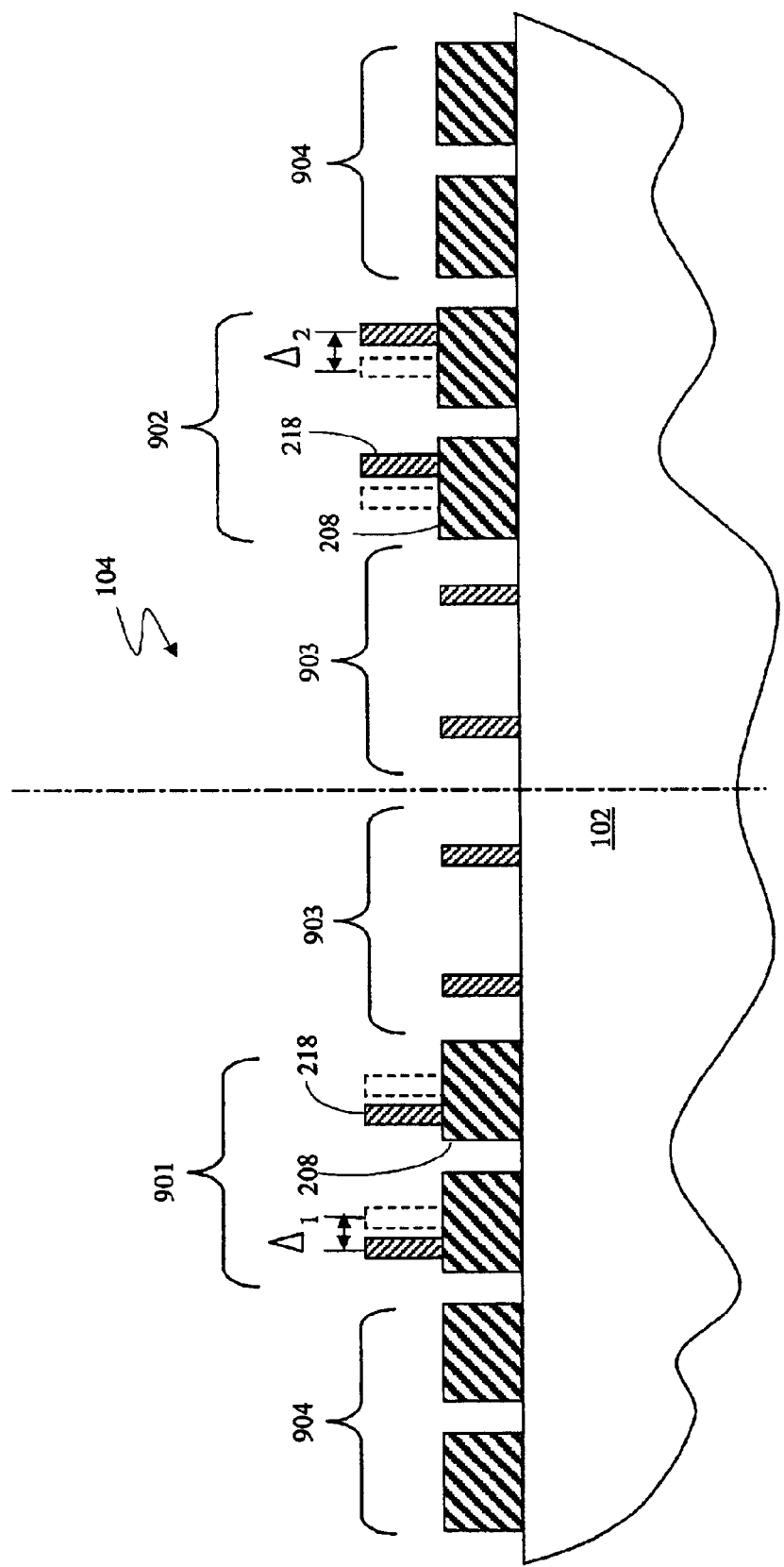
FIG. 9 depicts a portion of yet another exemplary periodic grating.

With reference to FIG. 9, in another exemplary embodiment, the geometry of ridges 208 and 218 are obtained in addition to overlay measurements. As depicted in FIG. 9, in the present embodiment, periodic grating 104 includes subfields 901, 902, 903, and 904. More particularly, in subfield 901, ridges 218 are shifted to the left of their symmetrically aligned position by an offset of $\Delta_1$. In subfield 902, ridges 218 are shifted to the right of their symmetrically aligned position by an offset of $\Delta_2$. As before, ridges 208 have the same period as ridges 218. In subfield 903, ridges 218 are patterned in isolation from ridges 208. In subfield 904, ridges 208 are patterned in isolation from ridges 218. In this manner, the geometry of ridges 208 can be obtained without interference from ridges 218, and the geometry of ridges 218 can be obtained without interference from ridges 208.

Figure 10:
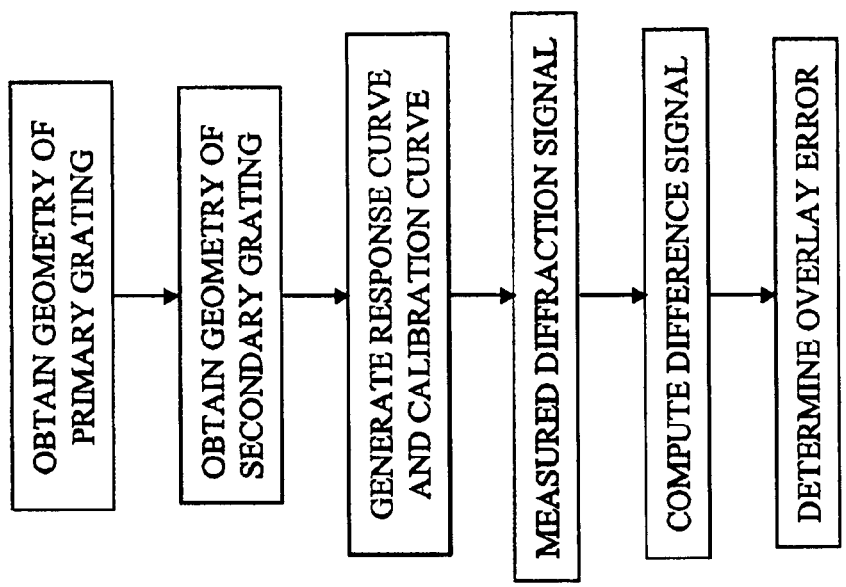
FIG. 10 is an exemplary flow chart of a process of obtaining overlay measurements.

With reference to FIG. 10, the process of obtaining overlay measurements for periodic grating depicted in FIG. 10 is depicted as a flow chart. As set forth in FIG. 10, the geometry of the primary grating, which have been depicted as ridges 208 (FIG. 9), and the secondary grating, which have been depicted as ridges 218 (FIG. 9), are obtained. More particularly, with reference to FIG. 9, in the present embodiment, geometry measurements for ridges 208 are obtained from subfields 904 in which ridges 208 are patterned in isolation from ridges 218. The geometry measurements for ridges 218 are obtained from subfields 903 in which ridges 218 are patterned in isolation from ridges 208.

With reference again to FIG. 3, the geometry of ridges 208 and 218 (FIG. 9) can be determined using optical metrology system 300. More particularly, as described above, to determine the geometry of ridges 208 and 218 (FIG. 9), optical metrology system 300 includes a signal-process module 3300, which compares the diffraction signal received by detector 320 to simulated-diffraction signals stored in a library 332. Each simulated-diffraction signal in library 332 is associated with a theoretical geometry of ridges 208 and 218 (FIG. 9). When a match is made between the diffraction signal received from detector 320 and one of the simulated-diffraction signals in library 332, the theoretical geometry associated with the matching simulated-diffraction signal is presumed to represent the actual geometry of ridges 208 and/or 218 (FIG. 9). It should be noted that an exact match is not necessary, a goodness of fit or similar error minimization criteria can be applied. Additionally, it should be noted that various tools and techniques can be used to determine the geometry of ridges 208 and 218 (FIG. 9).

After the geometry of ridges 208 and 218 (FIG. 9) are obtained, a response curve, which plots the diffraction versus various misalignments between ridges 208 and 218 (FIG. 9), is generated. Multiple response curves can be generated for a range of wavelengths of incident radiation, polarizations, and/or incidence angles. The desirable wavelength, polarization, and/or incidence angle can then be selected based on the response curves. Additionally, the response curve can be generated based on the obtained geometry of ridges 208 and 218 (FIG. 9). Alternatively, various response curves can be generated, then the obtained geometry of ridges 208 and 218 (FIG. 9) can be used to determine the appropriate response curve to use. Furthermore, as noted earlier, response curves can be generated empirically or computed through modeling.

After the response curve is generated, an intended asymmetric aligment (i.e., an intended offset) is selected that will correspond to zero misalignment. For example, a desirable intended offset would be a point on the response curve that is sensitive (i.e., the change in diffraction is large in response to a change in misalignment), and provides a wide range of unique solutions (i.e., a unique diffraction exists for a range of misalignment around the intended offset). Additionally, if multiple response curves are generated for a range of wavelengths of incident radiation, the criteria described for selecting an intended offset can be used to also select a desirable wavelength of incident radiation based on the response curves. Moreover, the response curves of more than one desirable wavelength can be used to extend the range of uniqueness and/or to increase sensitivity.

Once the intended offset is selected, a calibration curve can be generated by calculating the difference signals at each misalignment around the intended offset with reference to FIG. 3, one or more calibration curves can be generated and provided to metrology system 300 to obtain overlay measurements of periodic grating 104. The calibration curves can be stored on a storage media, such as a hard disk, CD, and the like, or remotely accessed by optical metrology system 300. Additionally, the calibration curves can be provided in various formats, such as a function, table of data, and the like.

In the present embodiment, to obtain overlay measurements, with reference to FIG. 9, diffraction signals are measured at subfield 901 and at subfield 902. As noted above, optical metrology system 300 (FIG. 3) can be used to obtain the diffraction signals.

With reference again to FIG. 10, after the diffraction signals are measured, a difference signal is computed. More particularly, the difference signal is the difference between the diffraction signals measured at subfield 901 and subfield 902 (FIG. 9).

After the difference signal is computed, the overlay error can be determined using the calibration curve. More particularly, the overlay error on the calibration curve with the same difference signal as the difference signal that is computed from the measured diffraction signals is assumed to be the actual overlay error.

The following example describes an exemplary process for determining the overlay error for a periodic grating. With reference again to FIG. 9, for the purpose of this example, assume that ridges 208 and 218 depict the ridges of a periodic grating that have been patterned on a wafer that is to be examined to obtain an overlay measurement (i.e., the amount of overlay error that may have resulted from the patterning process).

Assume for the purpose of this example that ridges 208 and 218 were formed as a resist on resist pattern, meaning that ridges 208 and 218 are formed from resist material. Resist-on-resist patterns are typically used to evaluate a stepper, which is a patterning tool. Assume for this example that period of ridges 208 and 218 is 1 micron, the linewidth of ridges 208 is 800 nm, the linewidth of ridges 218 is 200 nm, and the thickness (i.e., height) of ridges 208 and 218 is 500 nm.

Figure 11:
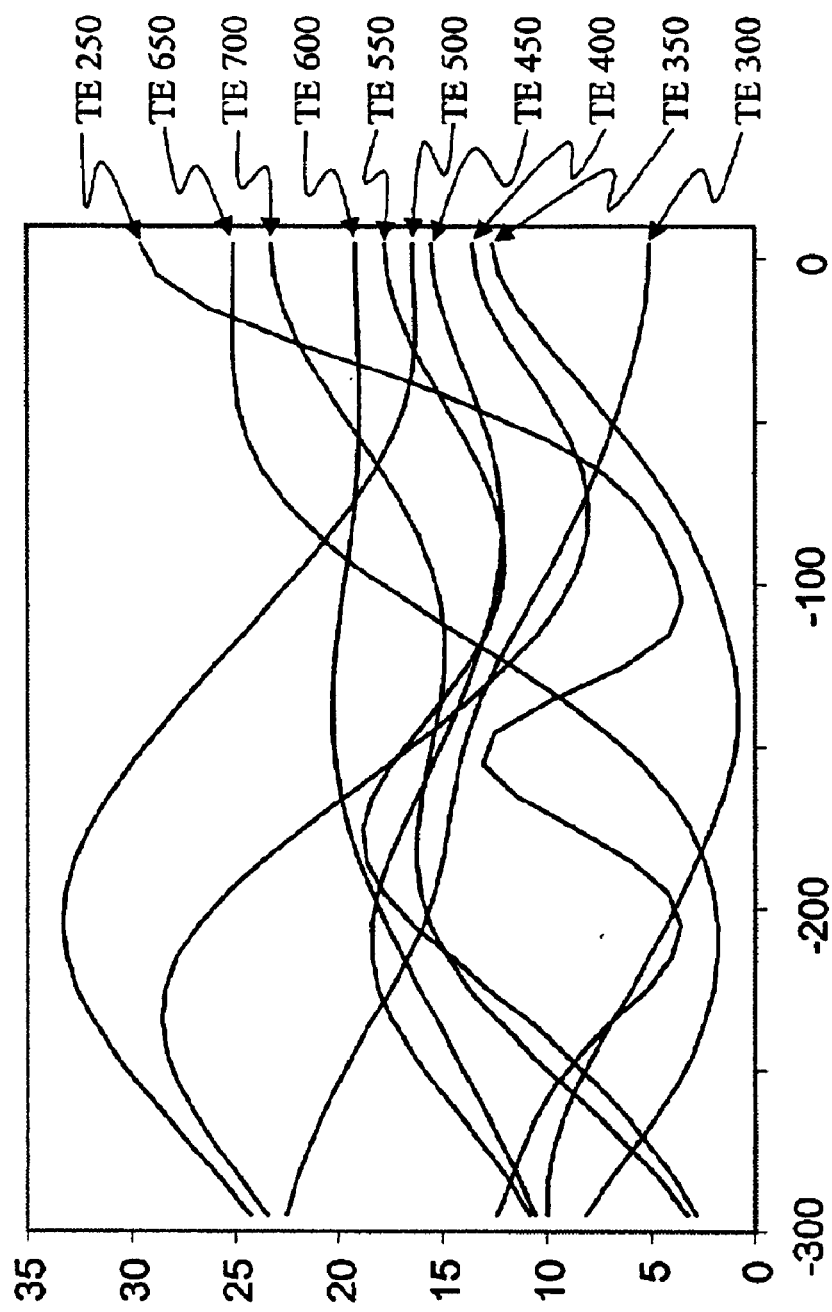
FIGS. 11 and 12 depict exemplary response curves.
Figure 12:
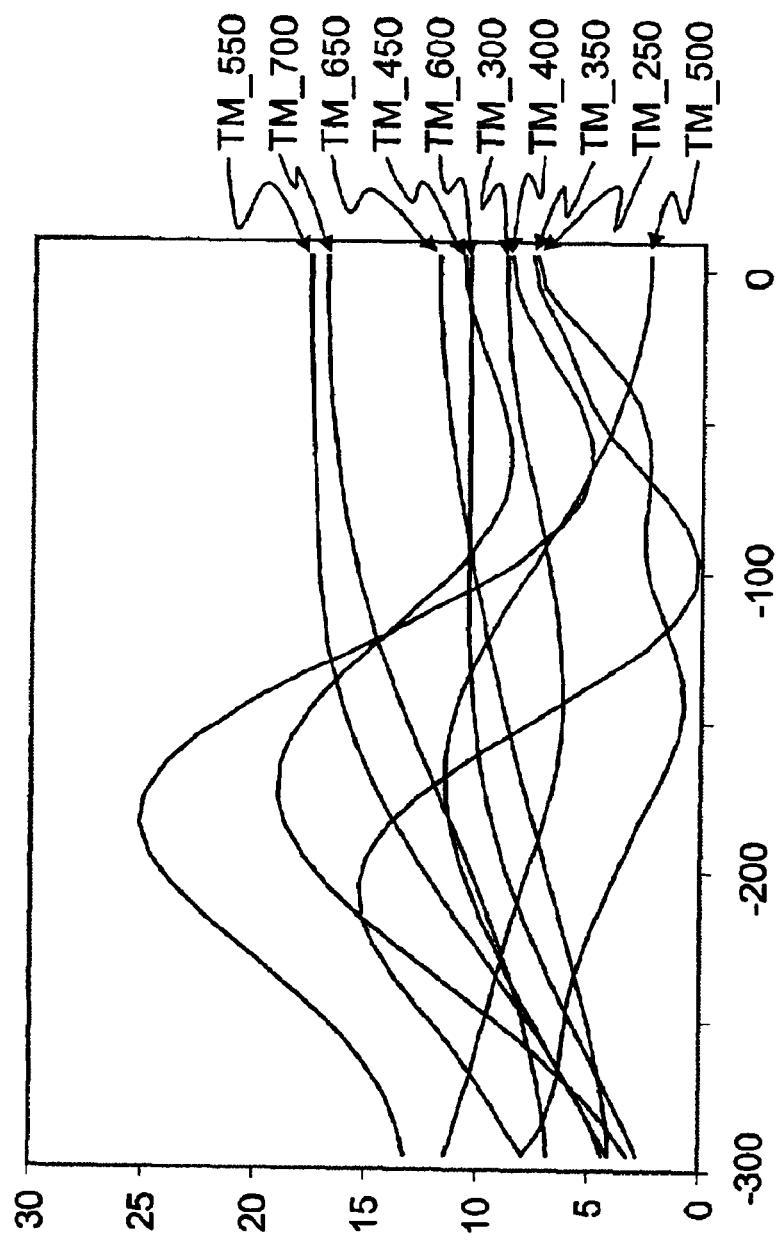

Response curves are generated for a range of misalignments between ridges 208 and 218. With reference to FIGS. 11 and 12, multiple response curves at various wavelengths are generated as a plot of misalignments (along the horizontal axis) versus the efficiency of the zero-order diffraction (along the vertical axis). FIG. 11 depicts the TE polarization, and FIG. 12 depicts the TM polarization. As depicted in FIGS. 11 and 12, in the present example, the range of misalignment is between –300 nm to 0 nm, wherein 0 nm corresponds to a symmetric alignment between ridges 208 and 218, meaning in the context of this example that the centers of ridges 208 and 218 are aligned. Additionally, in FIGS. 11 and 12, a response curve is depicted for each wavelength between a range of 250 nm to 700 nm in 50 nm increments.

As can be seen from FIGS. 11 and 12, between the range of –180 and –80 nm of misalignment, the response curve for the 400 nm wavelength has the greatest sensitivity. More particularly, between –180 and –80 nm of misalignment, the reflected efficiency drops from about 28% to 8% in TE and about 25% to 5% in TM. As such, 400 nm wavelength is selected as the desirable wavelength to use. Additionally, as there are unique reflected efficiencies at every misalignment in the range of –180 and –80 nm, –130 nm is selected as the intended offset.

Thus, with reference to FIG. 9, ridges 218 are intended to be formed asymmetrically aligned by an offset of 130 nm to the left of their symmetric alignment position in subfield 902 and 130 nm to the right of their symmetric alignment position in subfield 904. Thus, if ridges 218 are patterned without an overlay error, the centers of ridges 208 and 218 should be misaligned by an offset of 130 nm. More particularly, in subfield 902, the center of ridges 218 should be 130 nm to the left of the center of ridges 208. In subfield 904, the center of ridges 218 should be 130 nm to the right of the center of ridges 208.

Additionally, with reference to FIG. 11, if an incident radiation of 400 nm is used, then a reflected efficiency of the TE polarization should be 12% and the TM polarization should be 15%. Thus, when diffraction measurements are obtained from subfield 902 and there is no overlay error, then the measured diffraction should have a TE polarization of 12% and TM polarization of 15%.

Now assume that an overlay error of –10 nm occurs. With reference to FIG. 9, this corresponds to ridges 218 shifting to the left of their intended positions. Thus, the misalignments of ridges 218 in subfields 902 and 904 are –120 and –140 nm, respectively. The reflected efficiency at –120 and –140 nm of misalignment can be seen in FIGS. 11 and 12. The difference signal can then be calculated as the difference between the reflected efficiency at –120 and –140 nm of misalignment.

Figure 13:
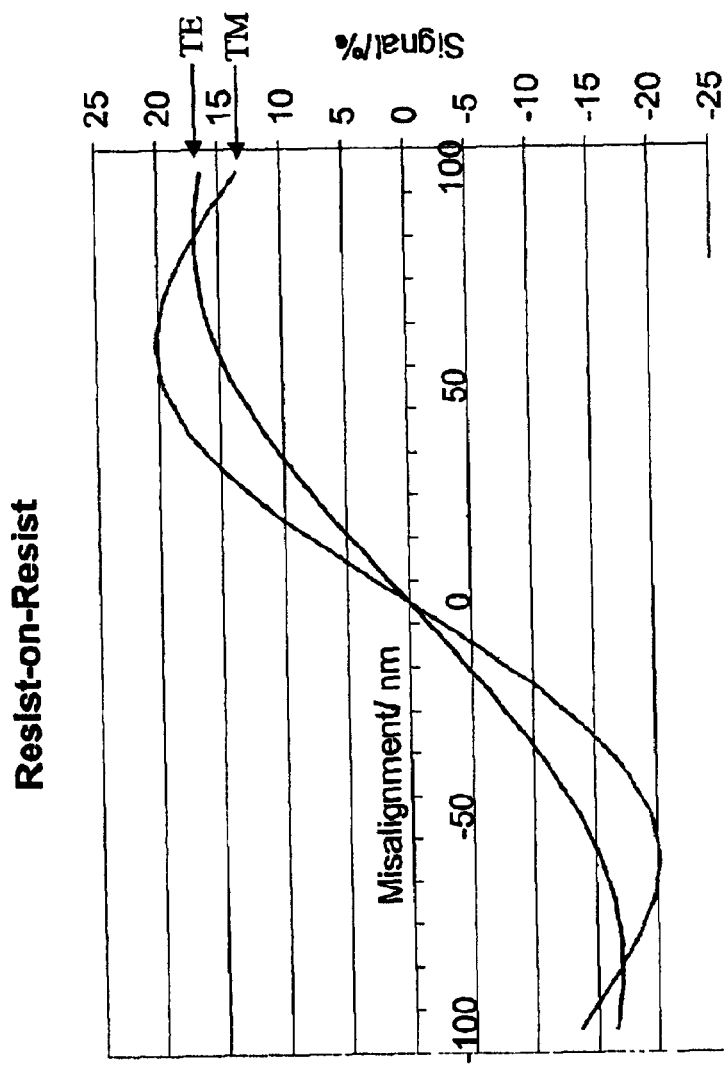
FIG. 13 depicts an exemplary calibration curve.

With reference to FIG. 13, a calibration curve of TE and TM polarization can be generated by computing the difference signal at various overlay errors. As depicted in FIG. 13, both of the calibration curves cross zero misalignment, which corresponds to zero overlay error. Additionally, between a range of plus and minus 50 nm of misalignment, thus over a total range of 100 nm of misalignment, both curves are sensitive (i.e., steep). More particularly, the TM calibration curve has a slope of about 0.4%/nm. Assuming an accuracy of 0.1% for a metrology tool, the overall accuracy is about 0.25 nm. Furthermore, between this range of misalignment, both calibration curves provide unique solutions. As such, one or both calibration curves can be used to detect the amount of overlay error as well as the direction of misalignment.

In the present example, only the intensity measurements have been used. However, as noted above, ellipsometric measurements, which include both phase and intensity ratio, can be obtained to further enhance sensitivity.

Thus far, including the previous example, a resist-on-resist structure has been assumed. As noted earlier, however, the process for obtaining overlay measurements can be applied to structures having various materials. For example, as will be described below, the process for obtaining overlay measurements can be applied to a resist-on-poly-silicon structures.

As such, with reference to FIG. 9, for the purpose of this example, assume that ridges 208 and 218 were formed as a resist-on-poly-silicon pattern, meaning that ridges 208 are formed from poly-silicon material and ridges 218 are formed from resist material. Assume for this example that the period of ridges 208 and 218 is 1 micron, the linewidth of ridges 208 is 800 nm, the linewidth of ridges 218 is 200 nm, the thickness of the poly-silicon is 200 nm, and the thickness of the resist used is 500 nm.

Figure 14:
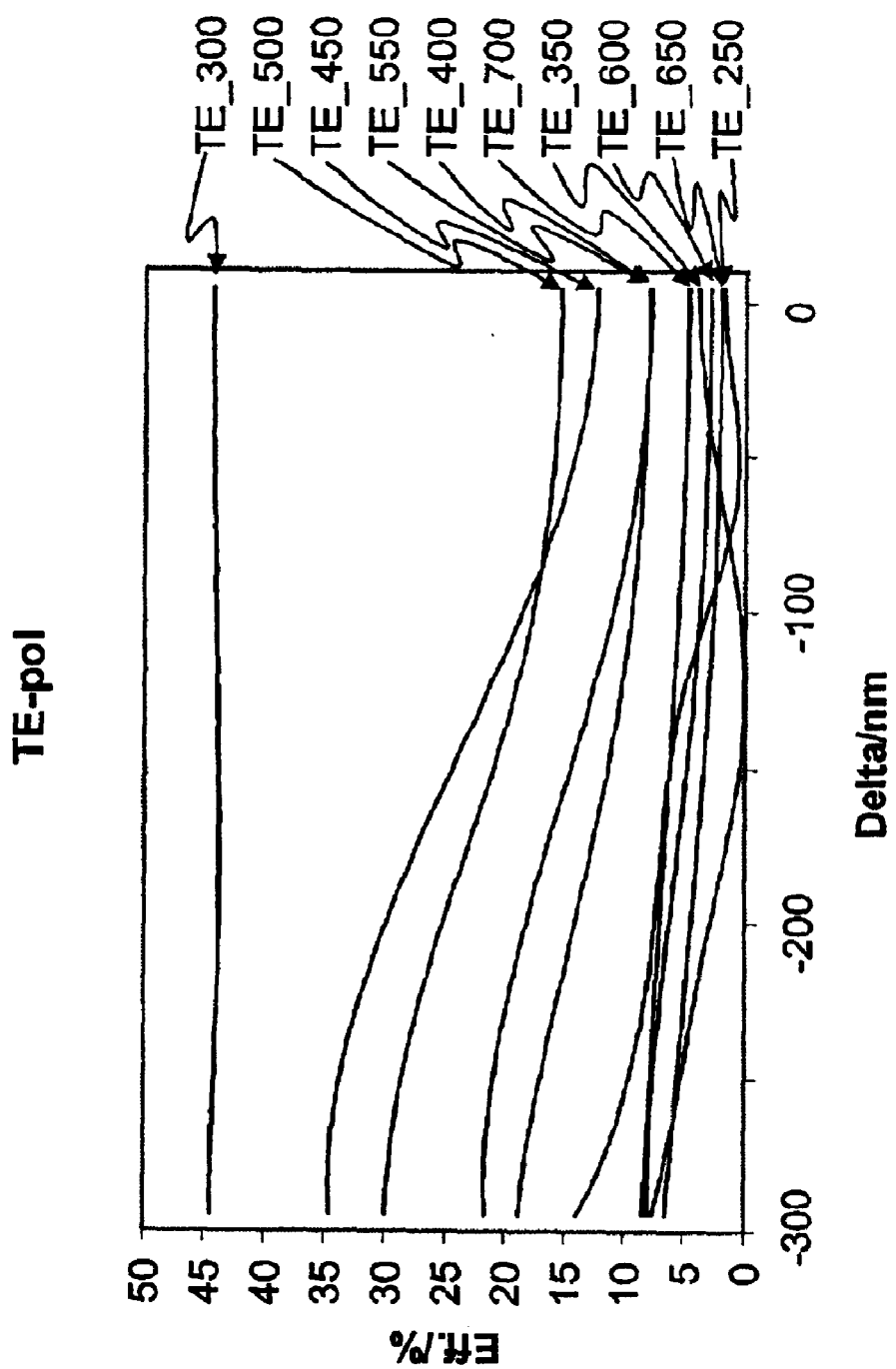
FIGS. 14 and 15 depict exemplary response curves.
Figure 15:
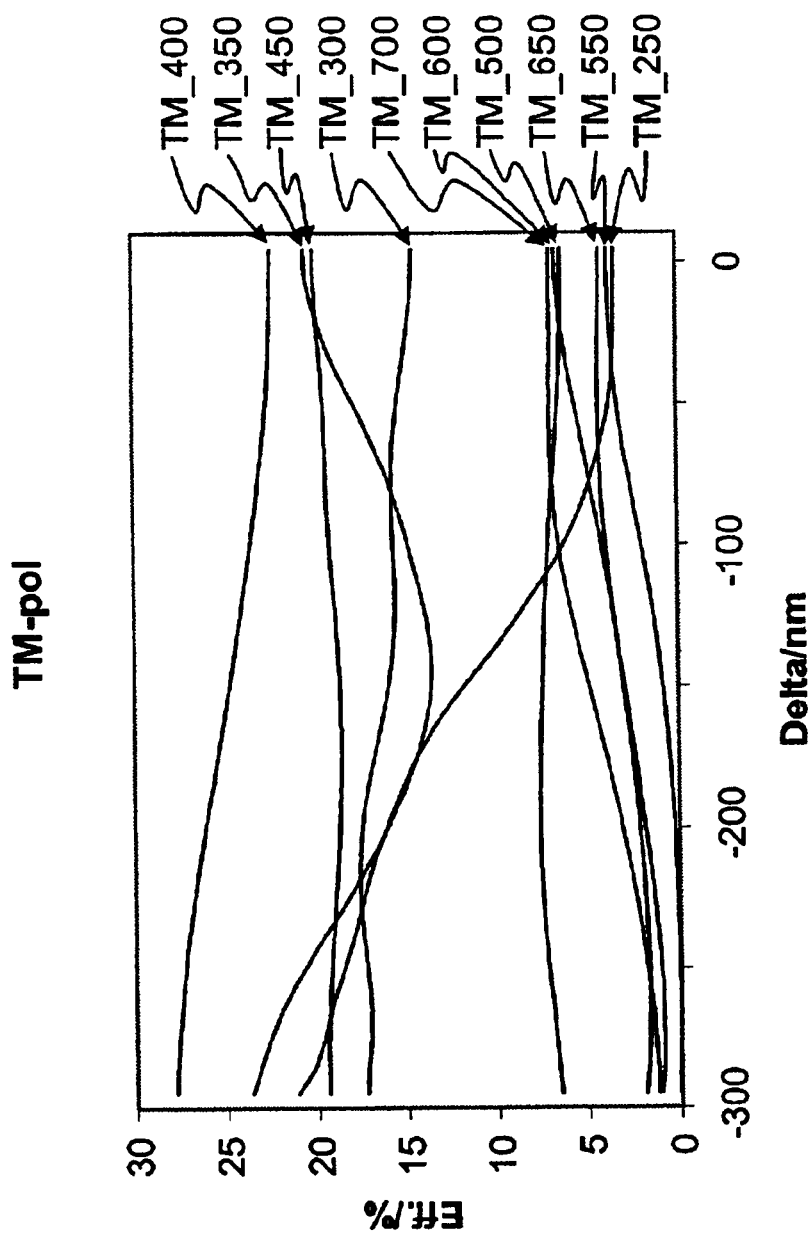

Similar to the previous example, response curves are generated for a range of misalignments between ridges 208 and 218. With reference to FIGS. 14 and 15, multiple response curves at various wavelengths are generated as a plot of misalignments (along the horizontal axis) versus efficiency of the zero-order diffraction (along the vertical axis). FIG. 14 depicts the TE polarization, and FIG. 15 depicts the TM polarization. As depicted in FIGS. 14 and 15, the range of misalignment is between −300 nm and 0 nm, where 0 nm corresponds to a symmetric alignment between ridges 208 and 218, meaning in the context of this example that the centers of ridges 208 and 218 are aligned. Additionally, in FIGS. 14 and 15, a response curve is depicted for each wavelength between a range of 250 nm to 700 nm in 50 nm increments.

As before, the response curves can be used to select a desirable intended offset and the desirable wavelength to use. Applying the criteria described earlier, in the present example, −150 nm is selected as the intended offset. However, in contrast to the previous example, in this example, two wavelengths are selected. More particularly, for the TE polarization, a wavelength of 450 nm is selected. For the TM polarization, a wavelength of 250 nm is selected.

Figure 16:
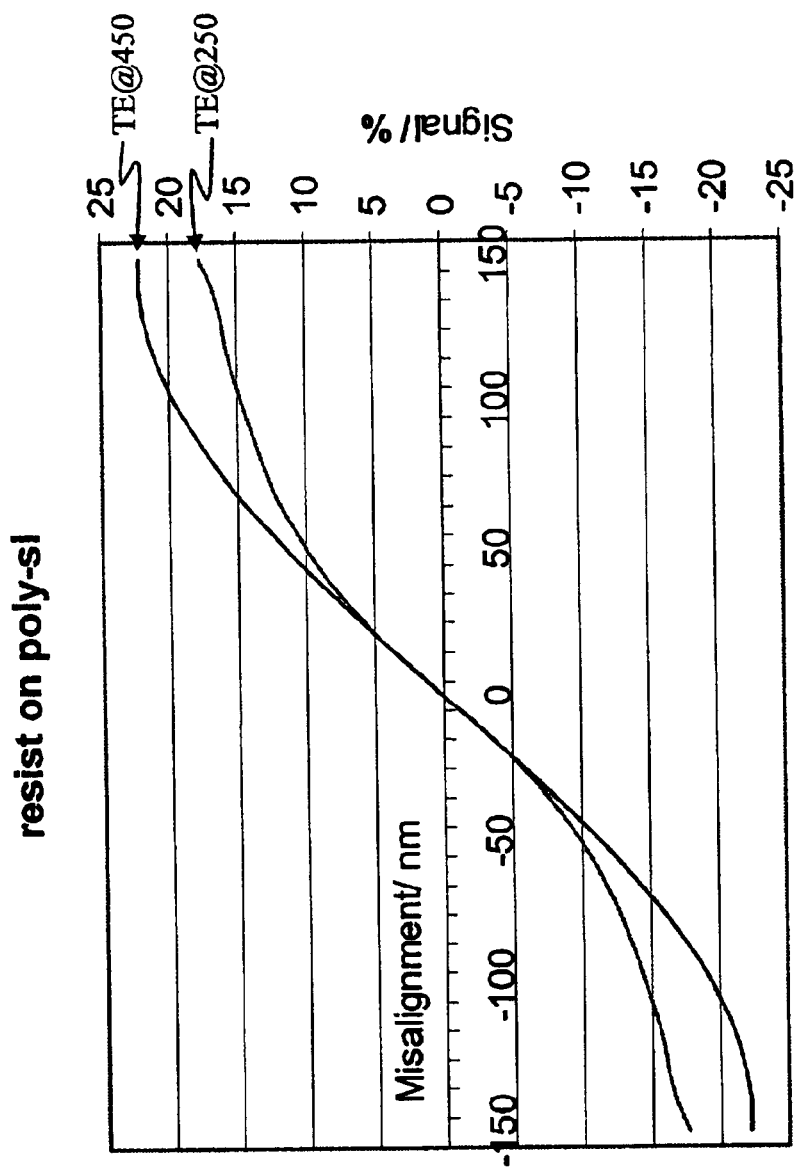
FIG. 16 depicts an exemplary calibration curve.

With reference to FIG. 16, using the process described above, a calibration curve of TE and TM polarization is generated based on the response curves. As before, both calibration curves cross zero misalignment, which corresponds to zero overlay error. In comparison to the previous example, the present calibration curves are less sensitive. More particularly, the TE calibration curve has a slope of about 0.2%/nm. Assuming again an estimated metrology tool accuracy of 0.1%, the overall accuracy is about 0.5 nm. In comparison to the previous example, the present calibration curves have a broader range. More particularly, both calibration curves provide unique solutions between a range of plus and minus 150 nm in misalignment for a total range of 300 nm.

Thus far, periodic grating 104 (FIG. 1) has been depicted as varying only in a single dimension. It should be recognized, however, that periodic grating 104 (FIG. 1) can vary in two dimensions, and that the process described above can apply to 3 dimensional overlay patterns.

Figure 17:
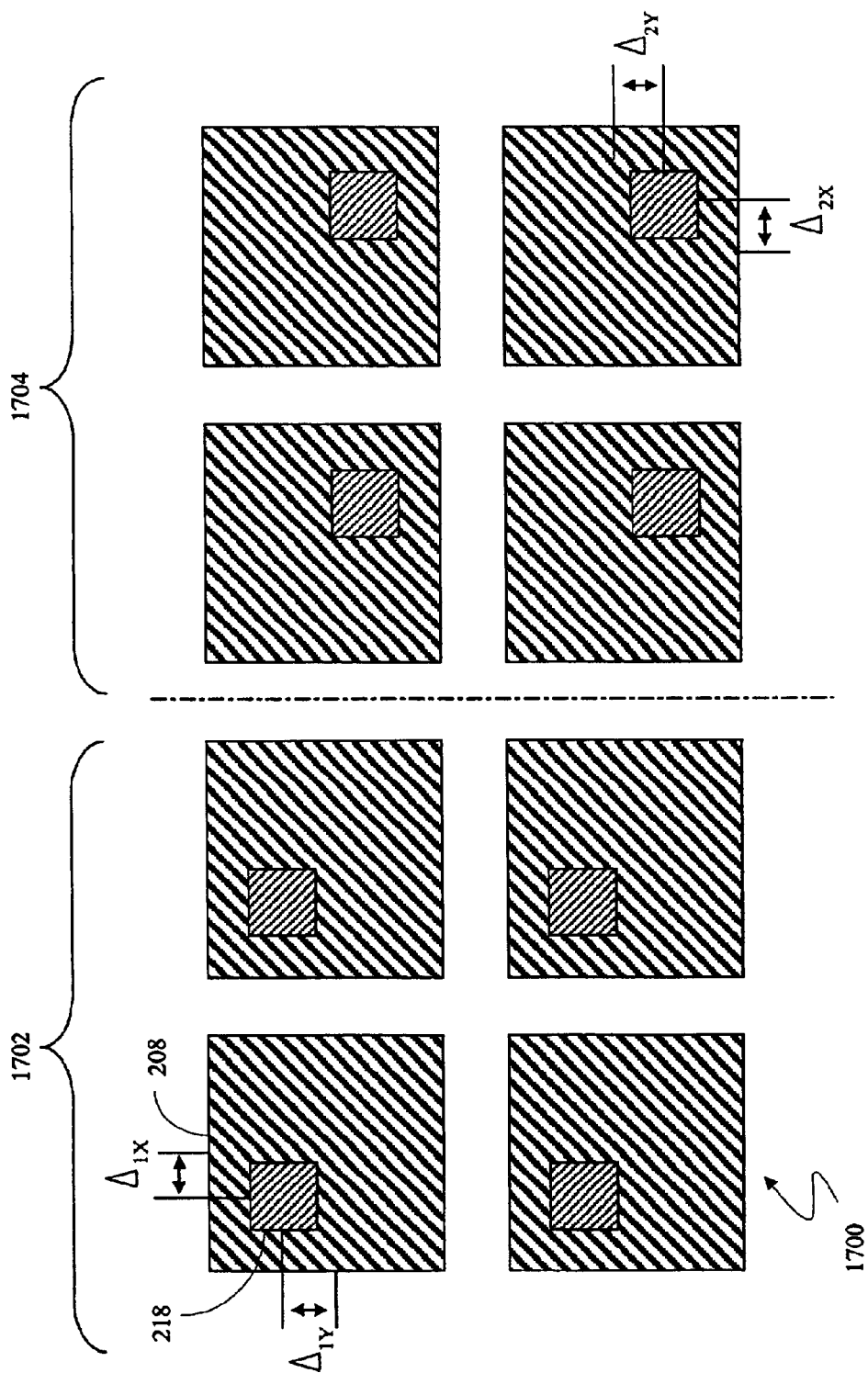
FIG. 17 depicts a top view of a portion of an exemplary periodic grating.

More particularly, with reference to FIG. 17, a top view of a periodic grating 1700 that varies in 2 dimensions is depicted. As depicted in FIG. 17, periodic grating 1700 includes a subfield 1702 and subfield 1704. In the present embodiment, subfield 1704 is configured as a mirror image of subfield 1702.

As also depicted in FIG. 17, ridges 208 and 218 are asymmetrically aligned. More particularly, in subfield 1702, ridges 208 and 218 are spaced with an intended horizontal offset of $\Delta_{1X}$ and an intended vertical offset of $\Delta_{1Y}$. In subfield 1704, ridges 208 and 218 are spaced with an intended horizontal offset of $\Delta_{2X}$ and an intended vertical offset of $\Delta_{2Y}$.

Similar to previous examples, response curves can be generated for a range of misalignments between ridges 208 and 218 to determine a desirable intended offset and wavelength to be used. A calibration curve can also be generated based on the response curves. In the present embodiment, a calibration curve for the horizontal and vertical offsets can be generated.

To obtain overlay measurements, diffraction signals are measured from subfield 1702 and subfield 1704. A difference signal is then calculated as the difference between the diffraction signals measured from subfield 1702 and subfield 1704. More particularly, a difference signal in the horizontal direction (i.e., a horizontal difference signal) can be calculated as $S_{HorizontalDiff} = S(\Delta_{1X}) - S(\Delta_{2X})$. A difference signal in the vertical direction (i.e., a vertical difference signal) can be calculated as $S_{VerticalDiff} = S(\Delta_{1Y}) - S(\Delta_{2Y})$. The difference signals can then be compared to the calibration curves to determine the amount and direction of misalignment.

In the previous examples, a normal incidence angle was presumed. However, as noted earlier, various incidence angles can be utilized, and more particularly a classical oblique incidence can be utilized.

For example, with reference to FIG. 3, for the sake of the present example, assume an angle of incidence $\theta_i$ of 65 degrees. With reference to FIG. 8, also assume for the sake of the present example that ridges 218 are formed on top of ridges 208, and that ridges 218 and 208 are formed from resist and poly-silicon material, respectively. It should be noted, however, that ridges 218 and 208 can be formed adjacent to each other and from various materials.

Figure 18:
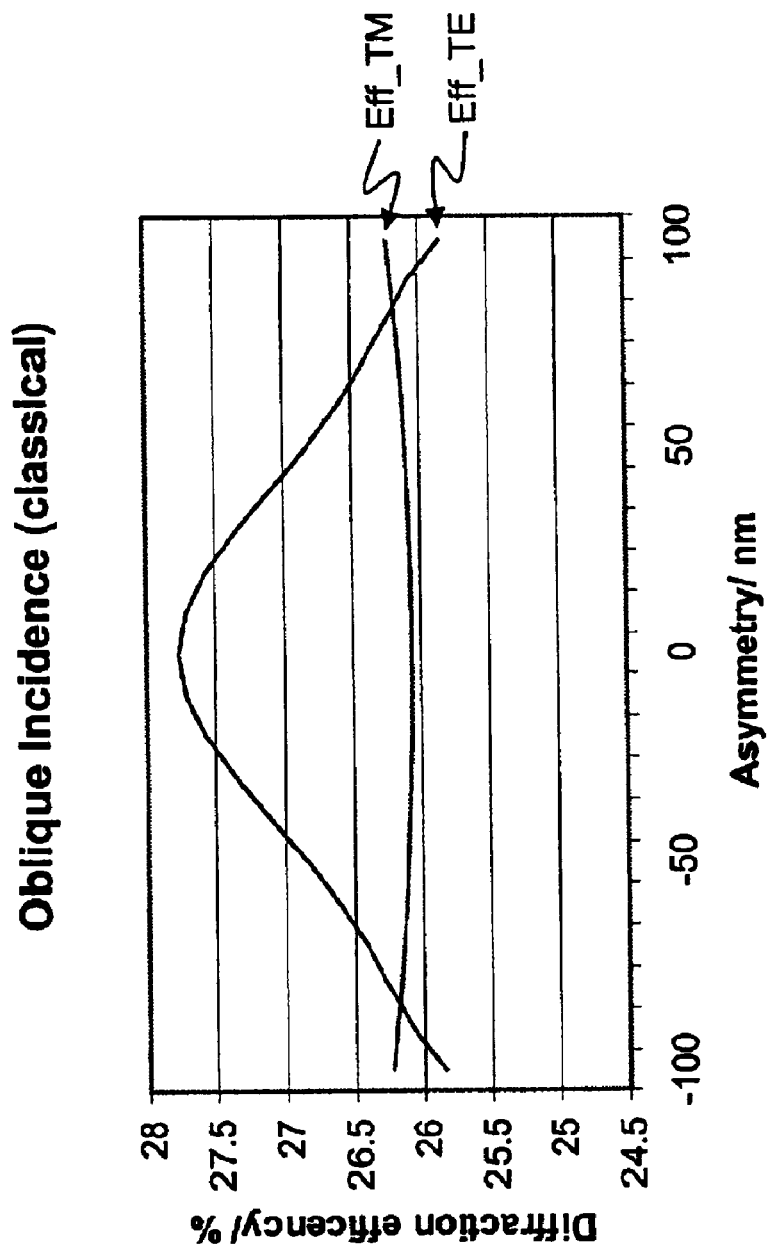
FIG. 18 depicts an exemplary response curve.

With reference to FIG. 18, a response curve of diffraction efficiency versus the offset between ridges 218 and 208 is depicted. More particularly, asymmetry of zero in FIG. 18 corresponds to the center of ridge 218 being positioned at the center of ridge 208 (FIG. 8). Asymmetry of negative 100 nm and positive 100 nm in FIG. 18 correspond to the center of ridge 218 being positioned 100 nm to the left or right, respectively, of the center of ridge 208.

Similar to FIG. 5, which presumed a normal angle of incidence, the response curve in FIG. 18 is symmetric about the point of symmetry (i.e., an asymmetry of zero). As such, the point of symmetry can be used to determine the existence of an overlay error, but the direction of misalignment cannot be determined solely based on the point of symmetry. As such, ridges 218 and 208 are asymmetrically aligned with an intended offset, and the zero-order diffraction signal is used to determine the amount and direction of misalignment.

Additionally, with reference to FIG. 3, thus far an azimuthal angle $\Phi$ (i.e., the angle between the plane of the incidence beam and the direction of the periodicity of the periodic grating) of zero has been presumed. It should be recognized, however, that various azimuthal angles can be utilized. More particularly, as will be described below, conical diffraction having a non-zero azimuthal angle can be utilized.

With reference to FIG. 19-A, in an exemplary embodiment, an azimuthal angle of 45 degrees is depicted. With reference to FIG. 19-B, azimuthal angles of 0 and 90 degrees are depicted. With reference to FIG. 20, a response curve of tan Ψ (i.e., the amplitude ratio) of the diffraction signal versus the asymmetry of ridges 218 and 208 (FIG. 8) is depicted for azimuthal angles 0, 45, and 90 degrees. With reference to FIG. 21, a response curve of cos Δ (phase difference) of the diffraction signal versus the asymmetry of ridges 218 and 208 (FIG. 8) is depicted for azimuthal angles 0, 45, and 90 degrees.

As can be seen from FIGS. 20 and 21, the tan Ψ and cos Δ in the diffraction signal is sensitive to the azimuthal angle. Additionally, for each azimuthal angle, the behavior of the tan Ψ response curve does not necessarily correspond to the cos Δ response curves. For example, at azimuthal angle 45, the tan Ψ response curve depicted in FIG. 20 is relatively sensitive compared to the cos Δ response curve depicted in FIG. 21. At azimuthal angle 0, the tan Ψ response curve depicted in FIG. 20 is relatively insensitive compared to the cos Δ response curve depicted in FIG. 21. At azimuthal angle 90, the tan Ψ curve depicted in FIG. 20 and the cos Δ response curve depicted in FIG. 21 appear to be insensitive relative to azimuthal angles 0 and 45.

As such, overlay errors can be detected using an azimuthal angle of about 45 degrees and the tan Ψ of the diffracted beam. More particularly, in the present example, the tan Ψ ranges from about 5.5 through 3.5 from 100 through 0 nm in deviations from symmetry. Thus, assuming that the accuracy of the data acquisition has an rms (root mean square) of 0.01, the accuracy of the offset error measurement can be better than 0.5 nm over a measurement range of 100 nm. It should be noted that this accuracy can be improved by optimizing certain parameters such as the wavelength used.

One advantage of using an azimuthal angle other than 0 and 90 degrees is that overlay measurements can be obtained in two coordinate directions without rotating the wafer. More particularly, with reference to FIG. 19-B, assume that periodic gratings 104A and 104B are formed on wafer 102 (FIG. 1). As noted above, at an azimuthal angle of 90 degrees, the tan Ψ curve and the cos Δ response curve are relatively insensitive. As such, as depicted in FIG. 19-B, after obtaining overlay measurements in the x-direction using periodic grating 104A, wafer 102 (FIG. 1) is rotated so that overlay measurements in the y-direction can be obtained using periodic grating 104B.

In contrast, as depicted in FIG. 19-A, when an azimuthal angle of about 45 degrees is used, overlay measurements in the x-direction can be obtained from periodic grating 104A, then overlay measurements in the y-direction can be obtained from periodic grating 104B without rotating wafer 102 (FIG. 1). As noted above, various azimuthal angles other than 45 degrees can be utilized.

Thus far, obtaining overlay measurements in one or two dimensions has been described. However, the tilt between two layers can also be obtained based on the overlay measurements obtained in one or two dimensions. More particularly, overlay measurements can be obtained for two metrology fields on a wafer that are situated a distance apart from each other. The tilt error arc can then be computed as the difference between the overlay measurements for the two metrology fields divided by the distance between the two metrology fields.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. A method of obtaining overlay measurements for a semiconductor wafer, the method comprising:
    forming a periodic grating on the wafer having:
        a first set of gratings,
        wherein the first set of gratings are formed on the wafer using a first mask, and
        a second set of gratings,
        wherein the second set of gratings are formed on the wafer using a second mask,
        wherein the first and second sets of gratings are intended to be formed on the wafer with an intended asymmetrical alignment when the first mask and second mask are in alignment;
    selecting a wavelength;
    measuring a diffraction signal of the first and second sets of gratings after the first and second sets of gratings are formed on the wafer using the selected wavelength; and
    determining a misalignment between the first and second sets of gratings formed on the wafer based on the measured diffraction signal.

2. The method of claim 1, wherein the measured diffraction signal is a zero-order diffraction.

3. The method of claim 2, wherein only the zero-order diffraction is measured.

4. The method of claim 1, wherein the diffraction signal is measured using an optical metrology system.

5. The method of claim 4, wherein the optical metrology system includes an ellipsometer.

6. The method of claim 4, wherein the optical metrology system includes a reflectometer.

7. The method of claim 1, wherein the diffraction signal is measured using an incident signal with a normal incidence angle.

8. The method of claim 1, wherein the diffraction signal is measured using an incident signal with an oblique incidence angle.

9. The method of claim 8, wherein the incident signal has an azimuthal angle of zero degrees.

10. The method of claim 8, wherein the incident signal has an azimuthal angle of about 45 degrees.

11. The method of claim 10, wherein measuring the diffraction signal includes:
    measuring the amplitude of the diffraction signal.

12. The method of claim 1 further comprising:
    generating a set of diffraction signals for a range of possible misalignments between the first and second sets of gratings,
    wherein each diffraction signal in the set corresponds to a different possible misalignment within the range of possible misalignments.

13. The method of claim 12 further comprising:
    generating a response curve of the correspondence between the different possible misalignments of the first and second sets of gratings and the set of diffraction signals.

14. The method of claim 13, wherein selecting a wavelength comprises:
generating a plurality of response curves using various wavelengths, polarizations, and/or incidence angles; and
selecting a desirable wavelength, polarization, and/or incidence angle based on the generated response curves.

15. The method of claim 12 further comprising:
determining the intended asymmetric alignment between the first and second sets of gratings based on the generated set of diffraction signals and range of possible alignments.

16. The method of claim 12, wherein the set of diffraction signals are generated empirically.

17. The method of claim 12, wherein the set of diffraction signals are generated using modeling.

18. The method of claim 12, wherein the determining the misalignment between the first and second sets of gratings comprises:
comparing the measured diffraction signal to the generated set of diffraction signals; and
determining the possible misalignment that corresponds to the diffraction signal from the generated set of diffraction signals that matches the measured diffraction signal.

19. The method of claim 1, wherein the periodic grating includes:
a first portion with the first and second sets of gratings having a first intended asymmetric alignment; and
a second portion with the first and second sets of gratings having a second intended asymmetric alignment,
wherein the first and second intended asymmetric alignments are opposite in direction.

20. The method of claim 19, wherein measuring a diffraction signal further comprises:
measuring a first diffraction signal from the first portion of the periodic grating; and
measuring a second diffraction signal from the second portion of the periodic grating.

21. The method of claim 20 further comprising:
computing a difference between the first and second diffraction signals.

22. The method of claim 20, wherein the periodic grating includes:
a third portion having only the first set of gratings; and
a fourth portion having only the second set of gratings.

23. The method of claim 22 further comprising:
obtaining the geometry of the first set of gratings in the third portion of the periodic grating; and
obtaining the geometry of the second set of gratings in the fourth portion of the periodic grating.

24. The method of claim 23, wherein the geometry of the first and second sets of gratings is obtained using an optical metrology system.

25. The method of claim 19 further comprising:
generating a set of diffraction signals for a range of possible misalignments between the first and second sets of gratings; and
generating a set of difference signals based on the generated set of diffraction signals,
wherein each difference signal in the set corresponds to the difference between two diffraction signals in the generated set of diffraction signals.

26. The method of claim 25 further comprising:
generating a calibration curve of the correspondence between the different possible alignments of the first and second sets of gratings and the set of difference signals.

27. The method of claim 25, wherein the determining the misalignment between the first and second sets of gratings comprises:
comparing the computed difference between the first and second difference signals to the generated set of difference signals; and
determining the possible misalignment that corresponds to the difference signal from the generated set of difference signals that matches the computed difference.

28. The method of claim 1,
wherein the first and second sets of gratings include a plurality of ridges that repeat at a periodic interval, and
wherein the ridges of the first and second sets of gratings alternate.

29. The method of claim 28,
wherein the ridges of the first and second sets of gratings include centerlines having a spacing between the centerlines of the ridges of the first and second sets of gratings, and
wherein the first and second sets of gratings are symmetrically aligned when the spacing between the centerlines is uniform and asymmetrically aligned when the spacing between the centerlines is non-uniform.

30. The method of claim 29, wherein the intended asymmetric alignment includes an offset from symmetrical alignment of the first and second sets of gratings.

31. The method of claim 30, wherein the offset is about a quarter of the periodic interval of the first and second sets of gratings.

32. The method of claim 1,
wherein the first and second sets of gratings include a plurality of ridges that repeat at a periodic interval, and
wherein the ridges of the second set of gratings are formed on the ridges of the first set of gratings.

33. The method of claim 32,
wherein the ridges of the first and second sets of gratings include centerlines, and
wherein the first and second sets of gratings are symmetrically aligned when the centerlines of the ridges of the first and second sets of gratings are aligned and asymmetrically aligned when the centerlines are not aligned.

34. The method of claim 33, wherein the intended asymmetric alignment includes an offset from symmetrical alignment of the first and second sets of gratings.

35. The method of claim 34, wherein the ridges of the second set of gratings includes a linewidth, and wherein the offset is about a quarter of the linewidth of the ridges of the second set of gratings.

36. The method of claim 1, wherein forming a periodic grating on the wafer comprises:
forming a periodic grating in a first metrology field on the wafer;
forming a periodic grating in a second metrology field on the wafer,
wherein the first and second metrology fields are separated by a distance on the wafer;
obtaining overlay measurements from the first and second metrology fields; and computing a tilt error are based on the obtained overlay measurements.

37. The method of claim 36, wherein the tilt error arc is computed as the difference between the overlay, measurements divided by the distance between the first and second metrology fields.

38. A method of obtaining overlay measurements for a semiconductor wafer using a periodic grating, the method comprising:

forming a first set of gratings of the periodic grating on the wafer;

forming a second set of gratings of the periodic grating on the wafer, wherein the first and second sets of gratings are formed using separate masks, and wherein the second set of gratings are intended to be formed on the wafer with an intended asymmetrical alignment from the first set of gratings when the separate masks are in alignment;

generating a set of diffraction signals at a selected wavelength for a range of possible misalignments between the first and second sets of gratings, wherein each of the diffraction signal in the generated set of diffraction signals corresponds to a possible misalignment between the first and second sets of gratings;

measuring a diffraction signal of the first and second sets of gratings after the first and second sets of gratings are formed on the wafer, wherein the diffraction signal is measured using the selected wavelength; and determining a misalignment between the first and second sets of gratings based on the measured diffraction signal and the generated set of diffraction signals.

39. The method of claim 38, wherein the determining the misalignment between the first and second sets of gratings comprises:

comparing the measured diffraction signal to the generated set of diffraction signals; and determining the possible misalignment that corresponds to the diffraction signal from the generated set of diffraction signals that matches the measured diffraction signal.

40. The method of claim 39 further comprising:

determining a misalignment between the first and second masks based on the determined misalignment between the first and second sets of gratings.

41. The method of claim 40, wherein the amount and direction of misalignment of the first and second masks corresponds to the amount and direction of misalignment of the first and second sets of gratings.

42. The method of claim 38, wherein the intended asymmetric alignment between the first and second sets of gratings is selected based on the generated set of diffraction signals and range of possible misalignments.

43. The method of claim 38, wherein the measured diffraction signal is a zero-order diffraction.

44. The method of claim 38 further comprising:

generating a plurality of sets of diffraction signals at various wavelengths, polarizations, and/or incidence angles.

45. The method of claim 44 further comprising:

selecting a desirable wavelength, polarization, and/or incidence angle based on the generated sets of diffraction signals.

46. The method of claim 38, wherein forming a first set of gratings and forming a second set of gratings comprise:

forming a first portion of the periodic grating having the first and second sets of gratings at a first intended asymmetric alignment;

forming a second portion of the periodic grating having the first and second sets of gratings at a second intended asymmetric alignment, wherein the first and second intended asymmetric alignments are opposite in direction.

47. The method of claim 46, wherein measuring a diffraction signal further comprises:

measuring a first diffraction signal from the first portion of the periodic grating;

measuring a second diffraction signal from the second portion of the periodic grating; and computing a difference signal based on the difference between the measured first and second diffraction signals.

48. The method of claim 47 further comprising:

generating a set of difference signals based on the generated set of diffraction signals;

comparing the computed difference signal to the generated set of difference signals; and determining the alignment that corresponds to the difference signal from the generated set of difference signals that matches the computed difference signal.

49. The method of claim 48 further comprising:

forming a third portion of the period grating having only the first set of gratings; and forming a fourth portion of the periodic grating having only the second set of gratings;

obtaining the geometry of the first set of gratings in the third portion of the periodic grating; and obtaining the geometry of the second set of gratings in the fourth portion of the periodic grating.

50. The method of claim 48, wherein the generated set of diffraction signals are generated based on the obtained geometry of the first and second sets of gratings.

51. The method of claim 48, wherein obtaining the geometry of the first set of gratings and the second set of gratings comprises:

comparing the measured diffraction signals to a library of simulated-diffraction signals, each simulated-diffraction signal having an associated theoretical geometry.

52. The method of claim 38, wherein the first and second sets of gratings include a plurality of ridges that alternate with a spacing between the ridges, wherein the first and second sets of gratings are symmetrically aligned when the spacing between the ridges of the first and second sets of gratings is uniform and asymmetrically aligned when the spacing is non-uniform.

53. The method of claim 38, wherein the first and second sets of gratings include a plurality of ridges with centerlines, wherein the ridges of the second set of gratings are formed on the ridges of the first set of gratings, and wherein the first and second sets of gratings are symmetrically aligned when the centerlines of the ridges of the first and second sets of gratings are aligned and asymmetrically aligned when the centerlines are not aligned.

54. The method of claim 38 further comprising:

forming a periodic grating in a first metrology field on the wafer;

forming a periodic grating in a second metrology field on the wafer separated by a distance from the first metrology field;

obtaining overlay measurements from the first and second metrology fields; and determining a tilt error are by dividing the difference between the overlay measurements by the distance between the first and second metrology fields.

55. A method of obtaining overlay measurements for a semiconductor wafer using a periodic grating formed on the wafer, the method comprising:

obtaining the wafer, wherein the period grating on the wafer comprises:

a first set of grating that were formed on the wafer using a first mask, a second set of gratings that were formed on the wafer using a second mask, wherein the first and second sets of gratings were intended to be formed on the wafer with an asymmetric alignment when the first mask and second mask are in alignment;

generating a set of diffraction signals at a selected wavelength for a plurality of possible misalignments between the first and second sets of gratings;

measuring a diffraction signal of the first and second sets of gratings from the obtained wafer, wherein the diffraction signal is measured using the selected wavelength, and wherein the measured diffraction signal is a zero-order diffraction;

comparing the measured diffraction signal to the generated set of diffraction signals; and determining an amount and direction of misalignment between the first and second sets of gratings on the obtained wafer based on the possible alignment that corresponds to the diffraction signal from the set of diffraction signals that matches the measured diffraction signal.

56. The method of claim 55 further comprising:

determining an amount and direction of misalignment between the first and second masks based on the determined amount and direction of misalignment between the first and second sets of gratings.

57. The method of claim 55, wherein the periodic grating on the wafer further comprises:

a first periodic grating oriented for obtaining overlay measurements in a first coordinate direction, and a second periodic grating oriented for obtaining overlay measurements in a second coordinate direction; and wherein measuring a diffraction signal further comprises:

measuring a first diffraction signal from the first periodic grating, and measuring a second diffraction signal from the second periodic grating without rotating the wafer.

58. The method of claim 57, wherein the measured diffraction signals and the generated diffraction signals have amplitude ratios, and wherein the amplitude ratios of the measured diffraction signals are compared with the amplitude ratios of the generated diffraction signals.

59. The method of claim 57, wherein the first periodic grating comprises a plurality of ridges oriented at about 45 degrees, and wherein the second periodic grating is a mirror-image of the first periodic grating.

60. The method of claim 57, wherein the diffraction signals are measured using an oblique and conical incident signal.

61. The method of claim 57, wherein the diffraction signals are measured using an incident signal with an azimuthal angle of about 45 degrees.

62. The method of claim 55, wherein the diffraction signal is measured using a normal incidence angle.

63. The method of claim 55, wherein the diffraction signal is measured using an oblique incidence angle with an azimuthal angle of zero degrees.

64. The method of claim 55, wherein the periodic grating comprises:

a first portion with the first and second sets of grating having a first asymmetric alignment; and a second portion with the first and second sets of grating having a second asymmetric alignment, wherein the first and second asymmetric alignments are opposite in direction.

65. The method of claim 64, wherein measuring a diffraction signal further comprises:

generating differences between pairs of diffraction signals from the generated set of diffraction signals, wherein a pair of diffraction signals for each generated difference correspond to two different possible misalignments of the first and second sets of gratings;

measuring a first diffraction signal from the first portion of the periodic grating;

measuring a second diffraction signal from the second portion of the periodic grating;

computing a difference between the measured first and second diffraction signals; and comparing the computed difference with the generated differences.

66. The method of claim 64, wherein the periodic grating further comprises:

a third portion having only the first set of gratings, and a fourth portion having only the second set of gratings;

obtaining the geometry of the first set of gratings in the third portion of the periodic grating; and obtaining the geometry of the second set of gratings in the fourth portion of the periodic grating, wherein the geometry of the first set of gratings and the second set of gratings are obtained by comparing the measured diffraction signals to a library of simulated-diffraction signals, each simulated-diffraction signal having an associated theoretical geometry.

67. The method of claim 55 further comprising:

a first metrology field on the wafer;

a second metrology field on the wafer separated by a distance from the first metrology field;

obtaining overlay measurements from the first and second metrology fields; and determining a tilt error are by dividing the difference between the overlay measurements by the distance between the first and second metrology fields.

68. The method of claim 55, wherein the first and second sets of gratings include a plurality of ridges that alternate with a spacing between the ridges, wherein the first and second sets of gratings are symmetrically aligned when the spacing between the ridges of the first and second sets of gratings is uniform and asymmetrically aligned when the spacing is non-uniform.

69. The method of claim 55, wherein the first and second sets of gratings include a plurality of ridges with centerlines, wherein the ridges of the second set of gratings are formed on the ridges of the first set of gratings, and wherein the first and second sets of gratings are symmetrically aligned when the centerlines of the ridges of the first and second sets of gratings are aligned and asymmetrically aligned when the centerlines are not aligned.

70. A system to obtain overlay measurements of a semiconductor wafer, the system comprising:

a periodic grating formed on the wafer comprising:
 a first set of gratings formed using a first mask,
 a second set of gratings formed using a second mask, and
 wherein the first and second sets of gratings are intended to be formed with an asymmetric alignment when the first mask and second mask are in alignment; and an optical metrology system comprising:
 a detector configured to measure a diffraction signal from the first and second sets of gratings using a selected wavelength, and
 a signal processing unit configured to determine a misalignment between the first and second sets of gratings based on the measured diffraction signal.

71. The system of claim 70, wherein the signal processing unit is configured to compare the measured diffraction signal to a set of diffraction signals generated for a plurality of possible alignments between the first and second sets of gratings.

72. The system of claim 70, wherein the periodic grating further comprises:

a first periodic grating oriented in a first coordinate direction; and a second periodic grating oriented in a second coordinate direction, wherein overlay measurements can be obtained in the first and second coordinate directions using the first and second periodic gratings without rotating the wafer.

73. The system of claim 72, wherein the first periodic grating comprises a plurality of ridges oriented at about 45 degrees, and wherein the second periodic grating is a mirror-image of the first periodic grating.

74. The system of claim 72, wherein the optical metrology system comprises:

a source configured to produce an oblique and conical incident signal.

75. The system of claim 70, wherein the optical metrology system comprises:

a source configured to produce a normal incident signal.

76. The system of claim 70, wherein the optical metrology system comprises:

a source configured to produce an incident signal having an oblique incidence angle and an azimuthal angle of zero degrees.

77. The system of claim 70, wherein the periodic grating comprises:

a first portion with the first and second sets of gratings having a first asymmetric alignment; and a second portion with the first and second sets of gratings having a second asymmetric alignment.

78. The system of claim 77, wherein the detector is configured to measure a first diffraction signal from the first portion of the period grating and a second diffraction signal from the second portion of the periodic grating, and wherein the signal processor is configured to determine the amount and direction of misalignment between the first and second masks used to form the first and second sets of gratings based on the measured first and second diffraction signals.

79. The system of claim 78, wherein the signal processor is configured to determine the alignment of the first and second sets of gratings by comparing the difference between the measured first and second diffraction signals to a set of difference signals generated for a plurality of possible misalignments between the first and second sets of gratings.

80. The system of claim 78, wherein the periodic grating further comprises:

a third portion having only the first set of gratings; and a fourth portion having only the second set of gratings.

81. The system of claim 80, wherein the optical metrology system comprises:

a library of simulated-diffraction signals having a set of theoretical geometry of the first and second sets of gratings;

wherein the detector is configured to measure a diffraction signal from the third portion and a diffraction signal from the fourth portion; and wherein the signal processing unit is configured to compare the measured diffraction signal to the simulated-diffraction signals to determine the geometry of the first and second sets of gratings.

82. The system of claim 70 further comprising:

a first metrology field on the wafer;

a second metrology field on the wafer separated by a distance from the first metrology field;

wherein the optical metrology system is configured to obtain overlay measurements from the first and second metrology fields and determine a tilt error are by dividing the difference between the overlay measurements by the distance between the first and second metrology fields.

83. The system of claim 70, wherein the first and second sets of gratings include a plurality of ridges that alternate with a spacing between the ridges; and wherein the first and second sets of gratings are symmetrically aligned when the spacing between the ridges of the first and second sets of gratings is uniform and asymmetrically aligned when the spacing is non-uniform.

84. The system of claim 70, wherein the first and second sets of gratings include a plurality of ridges with centerlines; wherein the ridges of the second set of gratings are formed on the ridges of the first set of gratings; and wherein the first and second sets of gratings are symmetrically aligned when the centerlines of the ridges of the first and second sets of gratings are aligned and asymmetrically aligned when the centerlines are not aligned.

85. A computer-readable storage medium containing computer executable instructions for causing a computer to obtain overlay measurements for a semiconductor wafer, comprising instructions for:

measuring a diffraction signal at a selected wavelength of a first set of grating and a second set of gratings of a periodic grating formed on the wafer, wherein the first set of gratings were formed using a first mask, the second set of gratings were formed using a second mask, and wherein the first and second sets of gratings were intended to be formed on the wafer with an asymmetric alignment when the first mask and second mask are in alignment;

generating a set of diffraction signals at the selected wavelength for a plurality of possible misalignments between the first and second sets of gratings;

determining a misalignment of the first and second sets of gratings formed on the wafer based on the measured diffraction signal and the generated set of diffraction signals; and determining the amount and direction of misalignment between the first and second masks based on the determined misalignment of the first and second sets of gratings formed on the wafer.

86. The computer-readable storage medium of claim 85, further comprising instructions for:

generating differences between pairs of diffraction signals from the generated set of diffraction signals, wherein a pair of diffraction signals for each generated difference corresponds to two different possible misalignments of the first and second sets of gratings;

measuring a first diffraction signal from a first portion of the periodic grating, wherein the first and second sets of gratings in the first portion have a first asymmetric alignment;

measuring a second diffraction signal from a second portion of the periodic grating, wherein the first and second sets of gratings in the second portion have a second asymmetric alignment;

computing a difference between the measured first and second diffraction signals; and comparing the computed difference with the generated differences.

87. The computer-readable storage medium of claim 85, further comprising instructions for:

obtaining the geometry of the first set of gratings; and obtaining the geometry of the second set of gratings, wherein the generated set of diffraction signals is generated based on the obtained geometry of the first and second sets of gratings.

88. The computer-readable storage medium of claim 87, further comprising instructions for:

measuring diffraction signals of the first set of gratings;

measuring diffraction signals of the second set of gratings; and comparing the measured diffraction signals to a library of simulated-diffraction signals having a set of theoretical geometry of the first and second sets of gratings.

89. The computer-readable storage medium of claim 88, wherein the diffraction signals of the first set of gratings are measured from a third portion of the grating having only the first set of gratings, and the diffraction signals of the second set of gratings are measured from a fourth portion of the grating having only the second set of gratings.

90. The computer-readable storage medium of claim 85, further comprising instructions for:

obtaining overlay measurements from a first metrology field on the wafer;

obtaining overlay measurements from a second metrology field on the wafer, wherein the first and second metrology fields are separated by a distance; and determining a tilt error are by dividing the difference in the obtained overlay measurements from the first and second metrology fields by the distance between the first and second metrology fields.

91. The computer-readable storage medium of claim 85, further comprising instructions for:

measuring a first diffraction signal from a first periodic grating;

determining the amount and direction of misalignment between the first and second mask in a first coordinate direction using the first measured diffraction signal;

measuring a second diffraction signal from a second periodic grating without rotating the wafer; and determining the amount and direction of misalignment between the first and second mask in a second coordinate direction using the second measured diffraction signal.

* * * * *